(12) United States Patent  (10) Patent No.: US 7,685,869 B2
Bonilla et al.  (45) Date of Patent: Mar. 30, 2010

(54) NANOINDENTER

(75) Inventors: Flavio Alejandro Bonilla, Santa Barbara, CA (US); Roger Proksch, Santa Barbara, CA (US); Jason Cleveland, Ventura, CA (US); Tim Sauter, Santa Barbara, CA (US)

(73) Assignee: Asylum Research Corporation, Santa Barbara, CA (US)

( * ) Notice: Subject to any disclaimer, the term of this patent is extended or adjusted under 35 U.S.C. 154(b) by 361 days.

(21) Appl. No.: 11/724,067

(22) Filed: Mar. 13, 2007

(65) Prior Publication Data

US 2007/0227236 A1   Oct. 4, 2007

Related U.S. Application Data

(60) Provisional application No. 60/782,072, filed on Mar. 13, 2006.

(51) Int. Cl.
*G01B 5/28* (2006.01)
*G01N 3/40* (2006.01)

(52) U.S. Cl. ............................................ 73/105; 73/81
(58) Field of Classification Search ............... 73/78, 73/81, 82, 105
See application file for complete search history.

(56) References Cited

U.S. PATENT DOCUMENTS

| 3,418,546 A | 12/1968 | Beavers et al. |
| 4,040,118 A | 8/1977 | Johnston |
| 4,104,901 A * | 8/1978 | Sidaway ..................... 73/81 |
| 4,237,989 A | 12/1980 | Lewis |
| 4,479,392 A | 10/1984 | Froeb et al. |
| 4,523,474 A | 6/1985 | Browne et al. |
| 4,550,617 A | 11/1985 | Fraignier et al. |
| 4,685,678 A | 8/1987 | Frederiksen |
| 4,694,687 A | 9/1987 | Bonin et al. |
| 4,699,000 A | 10/1987 | Lashmore et al. ............... 73/81 |
| 4,820,051 A | 4/1989 | Yanagisawa et al. ......... 356/378 |
| 4,848,141 A | 7/1989 | Oliver et al. .................... 73/81 |
| 4,922,444 A | 5/1990 | Baba |
| RE33,387 E | 10/1990 | Binnig |
| 4,970,374 A | 11/1990 | Ueda et al. |
| 5,065,103 A | 11/1991 | Slinkman et al. |
| 5,067,346 A | 11/1991 | Field ............................. 73/81 |
| 5,092,174 A | 3/1992 | Reidemeister et al. |
| 5,115,291 A | 5/1992 | Stokes |
| 5,128,671 A | 7/1992 | Thomas, Jr. |
| 5,134,886 A | 8/1992 | Ball |

(Continued)

FOREIGN PATENT DOCUMENTS

SU   1401347 A   *   6/1988

OTHER PUBLICATIONS

Cheng, Y.T., et al., "Scaling Relationships for Indentation Measurements," Philosophical Magazine A, vol. 82, No. 10, 2002, pp. 1821-1829.

(Continued)

*Primary Examiner*—Daniel S Larkin
(74) *Attorney, Agent, or Firm*—Law Ofc SC Harris

(57) ABSTRACT

A new type of indenter is described. This device combines certain sensing and structural elements of atomic force microscopy with a module designed for the use of indentation probes, conventional diamond and otherwise, as well as unconventional designs, to produce high resolution and otherwise superior indentation measurements.

1 Claim, 19 Drawing Sheets

U.S. PATENT DOCUMENTS

| | | | |
|---|---|---|---|
| 5,174,159 A | 12/1992 | Jacobsen et al. | |
| 5,193,383 A | 3/1993 | Burnham et al. | |
| 5,229,606 A | 7/1993 | Elings et al. | |
| RE34,331 E | 8/1993 | Elings et al. | |
| 5,255,562 A | 10/1993 | Yamamoto et al. | 73/160 |
| RE34,489 E | 12/1993 | Hansma et al. | |
| 5,305,633 A * | 4/1994 | Weissenbacher et al. | 73/82 |
| 5,329,808 A | 7/1994 | Elings et al. | |
| 5,359,879 A | 11/1994 | Oliver et al. | 73/7 |
| 5,383,354 A | 1/1995 | Doris et al. | |
| 5,400,647 A | 3/1995 | Elings | |
| 5,406,832 A | 4/1995 | Gamble et al. | |
| 5,412,980 A | 5/1995 | Elings et al. | |
| 5,415,027 A | 5/1995 | Elings et al. | |
| 5,461,907 A | 10/1995 | Tench et al. | |
| 5,463,897 A | 11/1995 | Prater et al. | |
| 5,481,908 A | 1/1996 | Gamble | |
| 5,497,656 A | 3/1996 | Kado et al. | |
| 5,504,338 A | 4/1996 | Marrian et al. | |
| 5,519,212 A | 5/1996 | Elings et al. | |
| 5,553,486 A | 9/1996 | Bonin | 73/105 |
| 5,557,156 A | 9/1996 | Elings | |
| 5,574,278 A | 11/1996 | Poirier | |
| 5,866,807 A | 2/1999 | Elings et al. | |
| 6,026,677 A | 2/2000 | Bonin | 73/105 |
| 6,252,557 B1 | 6/2001 | Plugge et al. | |
| 6,349,591 B1 | 2/2002 | Fretigny et al. | |
| 6,520,004 B1 | 2/2003 | Lin | |
| 6,642,129 B2 | 11/2003 | Liu et al. | |
| 6,694,829 B2 | 2/2004 | Chimura et al. | |
| 6,823,723 B2 | 11/2004 | Vandervorst et al. | |
| 6,867,443 B2 | 3/2005 | Liu et al. | |
| 6,884,999 B1 | 4/2005 | Yedur et al. | |
| 6,904,806 B2 | 6/2005 | Pryor | 73/597 |
| 6,945,097 B2 | 9/2005 | Jardret et al. | 73/81 |
| 6,993,959 B2 | 2/2006 | Shoelson | |

OTHER PUBLICATIONS

Chudoba, T., et al., "Determination of Mechanical Film Properties of a Bilayer System Due to Elastic Indentation Measurements with a Spherical Indenter," Thin Solid Films, 2000, pp. 377-378.

Chudoba, T., "Elastica 2.0—What is Elastica?" http://www.asmec.de/el-eval.html, 2002.

Cleveland, J.P., et al., "A Nondestructive Method for Determining the Spring Constant of Cantilever for Scanning Force Microscopy," Rev. Sci. Instrum., vol. 64, No. 2, Feb. 1993, pp. 403-405.

Dixson, R., et al., "Accurate Dimensional Metrology with Atomic Force Microscopy," Proceedings of SPIE, vol. 3998, 2000, pp. 362-368.

Doerner, M.F., et al., "A Method for Interpreting the Data from Depth-Sensing Indentation Instruments," J. Mater. Res., vol. 1, No. 4, Jul./Aug. 1986, pp. 601-609.

Hay, J.C., et al., "A Critical Examination of the Fundamental Relations Used in the Analysis of Nanoindentation Data," J. Mater. Res., vol. 14, No. 6, Jun. 1999, pp. 2296-2305.

Hansma, P.K., et al., "Scanning Tunneling Microscopy and Atomic Force Microscopy: Application to Boilogy and Technology," Science, vol. 242, Oct. 14, 1988, pp. 209-216.

Jardret, V., et al., "Scratch Durability of Automotive Clear Coatings: A Quantitative, Reliable and Robust Methodology," Journal of Coatings Technology, vol. 72, No. 907, Aug. 2000, pp. 79-88.

Jennett, N.M., et al., "Indicoat Final Report—Determination of Hardness and Modulus of Thin Films and Coatings by Nanoindentation," NPL Report MATC (A) 24, May 2001, 133 pages.

Lilleodden, E.T., et al., "In situ Imaging of μN Load Indents into GaAs," J. Mater. Res., vol. 10, No. 9, Sep. 1995, pp. 2162-2165.

Lu, C.J., et al., "Nanoindentation Hardness Tests Using a Point Contact Microscope," Journal of Tribology, vol. 116, Jan. 1994, pp. 175-180.

McElhaney, K.W., et al., "Determination of Indenter Tip Geometry and Indentation Contact Area for Depth-Sensing Indentation Experiments," J. Mater. Res., vol. 13, No. 5, May 1998, pp. 1300-1306.

Oliver, W.C., et al., "Measurement of Hardness at Indentation Depths as Low as 20 Nanometers," ASTM STP 889, Microindentation Techniques in Materials Science, 1986, pp. 90-108.

Oliver, W.C., et al., "Thin Film Characterization Using a Mechanical Properties Microprobe," Thin Solid Films, vol. 153, 1987, pp. 185-196.

Oliver, W.C., et al., "An Improved Technique for Determining Hardness and Elastic Modulus Using Load and Displacement Sensing Indentation Experiments," J. Mater. Res., vol. 7, No. 6, Jun. 1992, pp. 1564-1583.

Pethica, J.B., et al., "Tip Surface Interactions in STM and AFM," Physica Scripta, vol. T19, 1987, pp. 61-66.

Prater, C.B., et al., "TappingMode™ Imaging Applications and Technology," Digital Instruments, 1995, 8 pages.

Rugar, D., et al., "Atomic Force Microscopy," Physics Today, Oct. 1990, pp. 23-30.

Schwarzer, N., "Arbitrary Load Distribution on a Layered Half Space," Transactions of the ASME, vol. 122, Oct. 2000, pp. 672-681.

Stone, D.S., et al., "Elastic Rebound Between an Indenter and a Layered Specimen: Part I. Model," J. Mater. Res., vol. 13, No. 11, Nov. 1998, pp. 3207-3213.

Swadener, J.G., et al., "Measurement of Residual Stress by Load and Depth Sensing Indentation with Spherical Indenters," J. Mater. Res., vol. 16, No. 7, Jul. 2001, pp. 2091-2102.

Vanlandingham, M., et al., "Recent Progress in Nanoscale Indentation of Polymers Using the AFM," SEM IX Int'l Congress on Experimental Mechanics Proceedings, Orlando, Florida, Jun. 5-8, 2000, pp. 912-915.

Weihs, T.P., et al., "Mechanical Deflection of Cantilever Microbeams: A New Technique for Testing the Mechanical Properties of Thin Films," J. Mater. Res., vol. 3, No. 5, Sep./Oct. 1988, pp. 931-942.

Wickramasinghe, H.K., "Scanned-Probe Microscopes," Scientific American, Oct. 1989, pp. 98-105.

Wu, T.W., "Microscratch and Load Relaxation Tests for Ultra-Thin Films," J. Mater. Res., vol. 6, No. 2, Feb. 1991, pp. 407-426.

Yanagisawa, M., et al., "An Ultramicro Indentation Hardness Tester and Its Application to Thin Films," Lubrication Engineering, vol. 43, No. 1, Jan. 1987, pp. 52-56.

Bhattacharya, A.K., et al., "Finite Element Simulation of Indention Experiments," Int. J. Solid Structures, vol. 24, No. 9, (1998), pp. 881-891.

Bhattacharya, A.K., et al., "Analysis of Elastic and Plastic Deformation Associated with Indention Testing of Thin Films on Substrates," Int. J. Solid Structures, vol. 24, No. 12, (1988), pp. 1287-1298.

Bhushan, D., et al., "Nanoindentation Hardness Measurements Using Atomic Force Microscopy," Appl. Phys. Lett., vol. 64, No. 13, Mar. 28, 1994, pp. 1653-1655.

Bhushan, B., et al., "Nanoindentation and Picoindentation Measurements Using a Capacitive Transducer System in Atomic Force Microscopy," Philosophical Magazine A, vol. 74, No. 5, (1996), pp. 1117-1128.

Binning, G., et al., "Atomic Force Microscopy," Physical Review Letters, vol. 56, No. 9, Mar. 3, 1996, pp. 930-933.

Bogetti, T.A., et al., "Characterization of Nanoscale Property Variations in Polymer Composite Systems: 2. Numerical Modeling," Composites Part A, vol. 30 (1999), pp. 85-94.

Boschung, E., et al., "Energy Dissipation During Nanoscale Indentation of Polymers with an Atomic Force Microscope," Appl. Phys. Lett., vol. 64, No. 26, Jun. 27, 1994, pp. 3566-3568.

Chudoba, T., et al., "New Possibilities of Mechanical Surface Characterization with Spherical Indenters by Comparison of Experimental and Theoretical Results," Thin Solid Films 355-356 (1999), pp. 284-289.

Chudoba, T., et al., "Determination of Mechanical Properties of Graded Coatings Using Nanoindentation," Thin Solid Films 469-470 (2004), pp. 239-247.

Consiglio, R., et al., "The Nano-Scratch Tester (NST) as a New Tool for Assessing the Strength of Ultrathin Hard Coatings and the Mar Resistance of Polymer Films," Thin Solid Films 332 (1998), pp. 151-156.

Dirks, A.G., et al., "Mechanical Properties of Thin Alloy Films: Ultramicrohardness and Internal Stress," J. Appl. Phys., vol. 55, No. 12, Jun. 15, 1984, pp. 4248-4256.

Farhat, Z.N., et al., "Nanoindentation and Friction Studies on Ti-Based Nanolaminated Films," Surface and Coatings Technology, vol. 89 (1997), pp. 24-30.

Gao, H., et al., "Modeling Plasticity at the Micrometer Scale," Naturwissenschaften, vol. 86 (1999), pp. 507-515.

Gao, H., et al., "Mechanism-based Strain Gradient Plasticity—I. Theory," J. of Mechanics and Physics of Solids, vol. 47 (1999), pp. 1239-1263.

Geng, K., et al., "Nanoindentation Behavior of Ultrathin Polymeric Films," Polymer, vol. 46 (2005), pp. 11768-11772.

Goto, K., et al., "Micromachining with a Force Microscope Tip Assisted by Electrostatic Force," Rev. Sci. Instrum., vol. 67, No. 2, Feb. 1996, pp. 397-400.

Grigg, D.A., et al., "Tip-Sample Forces in Scanning Probe Microscopy in Air and Vacuum," J. Vac. Sci. Technol. A, vol. 10, No. 4, Jul./Aug. 1992, pp. 680-683.

Han, S.M., et al., "Determining Hardness of Thin Films in Elastically Mismatched Film-on-Substrate Systems Using Nanoindentation," Acta Materialia, vol. 54 (2006), pp. 1571-1581.

Heerens, W.C., "Application of Capacitance Techniques in Sensor Design," J. Phys. E. Sci. Instrum., vol. 19 (1986), pp. 897-906.

Hoh, J.H., et al., et al., "Friction Effects on Force Measurements with an Atomic Force Microscope," Langmuir, vol. 9 (1993), pp. 3310-3312.

Holman, A.E., et al., "Using Capacitive Sensors for in situ Calibration of Displacements in a Piezo-Driven Translation Stage of an STM," Sensors and Actuators A, vol. 36 (1993), pp. 37-42.

Huang, Y., et al., "Mechanism-based Strain Gradient Plasticity—II. Analysis," J. of Mechanics and Physics of Solids, vol. 48 (2000), pp. 99-128.

Huang, Y., et al., "Comparison of Mechanical Properties of $Ni_3Al$ Thin Films in Disordered FCC and Ordered $Ll_2$ Phases," Acta Materialia, vol. 49 (2001), pp. 2853-2861.

Joyce, S.A., et al., "A New Force Sensor Incorporating Force-Feedback Control for Interfacial Force Microscopy," Rev. Sci. Instrum., vol. 62, No. 3, Mar. 1991, pp. 710-715.

Kulkarni, A.V., et al., "Nano/Picoindentation Measurements on Single-Crystal Aluminum Using Modified Atomic Force Microscopy," Material Letters, vol., 29 (1996), pp. 221-227.

Li, X., et al., "A Review of Nanoindentation Continuous Stiffness Measurements Technique and Its Applications," Materials Characterization, vol. 48 (2002), pp. 11-36.

Li, X., et al., "Micro/Nanomechanical and Tribological Studies of Bulk and Thin-Film Materials Used in Magnetic Recording Heads," Thin Solid Films 398-399 (2001), pp. 313-319.

Linss, V., et al., "Mechanical Properties of Thin Films in the Ternary Triangle B-C-N," Surface and Coatings Technology, 163-164 (2003), pp. 220-226.

Linss, V., et al., "Mechanical Properties of a Graded B-C-N. Sputtered Coating with Varying Young's Modulus: Deposition, Theoretical Modelling and Nanoindentation," Surface and Coatings Technology, vol. 195 (2004), pp. 287-297.

Liu, Z., et al., "Study of Plowing and Friction at the Surfaces of Plastic Deformed Metals," Tribology Int'l, vol. 35 (2002), pp. 511-522.

Manne, S., et al., "Imaging Metal Atoms in Air and Water Using the Atomic Force Microscope," Appl. Phys. Lett., vol. 56, No. 18, Apr. 30, 1990, pp. 1758-1759.

Mate, C.M., "Nanotribology Studies of Carbon Surfaces by Force Microscopy," Wear, vol. 168 (1993), pp. 17-20.

Newey, D., et al., "An Ultra-Low-Load Penetration Hardness Tester," J. Phys. E., Sci. Instrum., vol. 15 (1982), pp. 119-122.

Nishibori, M., et al., "Ultra-Microhardness of Vacuum-Deposited Films I: Ultra-Microhardness Tester," Thin Solid Films, vol. 48 (1978), pp. 325-331.

Nix., W.D., et al., "Indentation Size Effects in Crystalline Materials: A Law for Strain Gradient Plasticity," J. Mech. Phys. Solids, vol. 46, No. 3 (1998), pp. 411-425.

Oliver, W.C., et al., "Measurements of Hardness and Elastic Modulus by Instrument Indentation: Advances in Understanding and Refinements to Methodology," J. Mater. Res., vol. 19, No. 1, Jan. 2004, pp. 3-20.

Oliver. W.C., "Alternative Technique for Analyzing Instrumented Indentation Data," J. Mater. Res., vol. 16, No. 11, Nov. 2001, pp. 3202-3206.

Panich, N., et al., "Effect of Penetration Depth on Indentation Response of Soft Coatings on Hard Substrates: A Finite Element Analysis," Surface and Coatings Technology, vol. 182 (2004), pp. 342-350.

Pharr, G.M., "Measurement of Mechanical Properties by Ultra-Low Load Indentation," Mat. Sci. and Engineering A, vol. 253 (1998), pp. 151-159.

Randall, N.X., et al., "Nanoscratch Tester for Thin Film Mechanical Properties Characterization," Rev. Sci. Instrum., vol. 71, No. 7, Jul. 2000, pp. 2796-2799.

Saha, R., et al., "Indentation of a Soft Metal Film on a Hard Substrate: Strain Gradient Hardening Effects," J. of Mech. and Physics of Solids, vol. 49 (2001), pp. 1997-2014.

Saha, R., et al., "Soft Films on Hard Substrates—Nanoindentation of Tungsten Films on Sapphire Substrates," Mat. Sci and Engineering A 319-321 (2001), pp. 898-901.

Saha, R., et al., "Effects of the Substrate on the Determination of Thin Film Mechanical Properties by Nanoindentation," Acta Materialia, vol. 50 (2002), pp. 23-28.

Schwarzer, N., et al., "Investigation of Ultra Thin Coatings Using Nanoindentation," Surface and Coatings Technology, vol. 200 (2005), pp. 5566-5580.

Schwarzer, N., et al., "On the Evaluation of Stresses in Coated Materials During Nanoindentation with Sharp Indenters," Surface and Coatings Technology, vol. 200 (2005), pp. 4220-4226.

Schwarzer, N., et al., "Contact Modelling in the Vicinity of an Edge," Surface and Coatings Technology, 146-147 (2001), pp. 371-377.

Schwarzer, N., et al., "Comparison Between Analytical and FEM Calculations for the Contact Problem of Spherical Indenters on Layered Materials," Thin Solid Films, vol. 270 (1995), pp. 279-282.

Schwarzer, N., et al., "The Elastic Field in a Coated Half-Space Under Hertzian Pressure Distribution," Surface and Coatings Technology, vol. 114 (1999), pp. 292-304.

Schwarzer, N., "Analysing Nanoindentation Unloading Curves Using Pharr's Concept of the Effective Indenter Shape," Thin Solid Films, vol. 494 (2005), pp. 168-172.

Schwarzer, N., et al., "Investigation of Coating Substrate Compounds Using Inclined Spherical Indentation," Surface and Coatings Technology 116-119 (1999), pp. 244-252.

Schwarzer, N., et al., "The Analytical Solution of the Contact Problem of Spherical Indenters on Layered Materials: Application for the Investigation of TiN Films on Silicon," Thin Solid Films, vol. 270 (1995), pp. 371-375.

Schwarzer, N., et al., "Adhesion and Elastic Contact Stresses of Coating/Substrate Systems Under Normal and Tangential Loads," Surface and Coatings Technology, 74-75 (1995), pp. 97-103.

Schwarzer, N., et al., "Determination of Mechanical Properties of Thin Films: A Theoretical Feasibility Study," Surface and Coatings Technology, vol. 60 (1993), pp. 396-400.

Sheiko, S.S., et al., "Evaluation of the Probing Profile of Scanning Force Microscopy Tips," Ultramicroscopy, vol. 53 (1994), pp. 371-380.

Sjostrom, H., et al., "Superhard and Elastic Carbon Nitride Thin Films Having Fullerenelike Microstructures," Phy. Rev. Lett., vol. 75, No. 7, Aug. 14, 1995, pp. 1336-1339.

Sun, Y., et al., "Finite Element Analysis of the Critical Ratio of Coating Thickness to Indentation Depth for Coating Property Measurements by Nanoindentation," Thin Solid Films, vol. 258 (1995), pp. 198-204.

Sun, Y., et al., "Indenter Tip Radius and Load Frame Compliance Calibration Using Nanoindentation Loading Curves," Philosophical Magazine Letters, vol. 79, No. 9 (1999), pp. 649-658.

Syed Asif, S.A., et al., "Quantitative Imaging of Nanoscale Mechanical Properties Using Hybrid Nanoindentation and Force Modulation," J. Appl. Phy., vol. 90, No. 3, Aug. 1, 2001, pp. 1192-1200.

Tang, K.C., et al., "Comparison Between an Elastic-Perfectly Plastic Finite Element Model and a Purely Elastic Analytical Model for a Spherical Indenter on a Layered Substrate," Thin Solid Films, vol. 300 (1997), pp. 177-188.

Tsou, C., et al., "Interfaces Friction Effect of Sliding Contact on Nanoindentation Test," Sensors and Actuators A, vol. 117 (2004), pp. 309-316.

Tsukamoto, Y., et al., "Mechanical Properties of Thin Films: Measurements of Ultramicroindentation Hardness, Young's Modulus and Internal Stress," Thin Solid Films, vol. 154 (1987), pp. 171-181.

Uelzen, T., et al., "Mechanical and Electrical Properties of Electroplated Copper for MR-Imaging Coils," Microsyst Technol., vol. 12 (2005), pp. 343-351.

Vanlandingham, M.R., et al., "Characterization of Nanoscale Property Variations in Polymer Composite Systems: 1. Experimental Results," Composites: Part A 30 (1999), 75-83.

Vanlandingham, M.R., et al., "Measuring Tip Shape for Instrumented Indentation Using Atomic Force Microscopy," Meas. Sci. Technol., vol. 16 (2005), pp. 2173-2185.

Van Vliet, K.J., et al., "Direct Measurement of Indentation Frame Compliance," J. Mater. Res., vol. 19, No. 1, Jan. 2004, pp. 325-331.

Vlassak, J.J., et al., "Measuring the Elastic Properties of Anisotropic Materials by Means of Indentation Experiments," J. Mech. Phys. Solids, vol. 42, No. 8 (1994), pp. 1223-1245.

Warmack, R.J., et al., "Friction Effects in the Deflection of Atomic Force Microscope Cantilevers," Rev. Sci. Instrum., vol. 65, No. 2, Feb. 1994, pp. 394-399.

Wierenga, P.E., et al., "Ultramicoindentation Apparatus for the Mechanical Characterization of Thin Films," J. Appl. Phys., vol. 55, No. 12, Jun. 15, 1984, pp. 4244-4247.

Wierenga, P.E., et al., "Ultramicrohardness Experiments on Vapour-Deposited Films of Pure Metals and Alloys," Thin Solid Films, vol. 119 (1984), pp. 375-382.

Zhang, F., et al., "Indentation of a Hard Film on a Soft Substrate: Strain Gradient Hardening Effects," Int'l J. of Plasticity, vol. 23 (2006), pp. 25-43.

International Search Report and Written Opinion for International Application No. PCT/US07/06379, mailed Dec. 21, 2007.

Asif, S.A.S., et al., "Nanoindentation and Contact Stiffness Measurement Using Force Modulation with a Capacitive Load-Displacement Transducer," Review of Scientific Instruments, May 1999, pp. 1-6.

Bhushan, B., et al., "Nanotribology: friction, wear and lubrication at the atomic scale," Nature, vol. 374, No. 13, Apr. 1995, pp. 607-616.

Briscoe, B.J., et al., "Nano-indentation of Polymeric Surfaces," J. Phys. D. Appl. Phys., vol. 31, No. 19, 1998, pp. 2395-2405.

Dao, M., et al., "Computational Modeling of the Forward and Reverse Problems in Instrumented Sharp Indentation," Acta Mater. vol. 49, 2001, pp. 3899-3918.

Huber, N., et al., "Identification of Elastic-Plastic Material Parameters from Pyramidal Indentation of Thin Films," Proc. Roy. Soc. Lond. A, vol. 458, 2002, pp. 1593-1620.

Vanlandingham, M.R., "Review of Instrumented Indentation," J. Res. Nat'l Inst. Stand. Technol., vol. 108, No. 4, 2003, pp. 249-265.

Vanlandingham, M.R., et al., "Nanoindentation of Polymers: An Overview," Molecular Symposia, vol. 167, Advances in Scanning Probe Microscopy of Polymers, Wiley-VCH Verlag GmbH, Germany, 2001, pp. 15-43.

* cited by examiner

NANOINDENTER

RELATED APPLICATION

This application claims priority to U.S. Provisional Patent Application No. 60/782,072, filed Mar. 13, 2006, entitled "Nanoindenter," which application is incorporated by referenced herein in its entirety.

BACKGROUND OF THE INVENTION

An AFM is a device used to produce images of surface topography (and other sample characteristics) based on information obtained from rastering a sharp probe on the end of a cantilever relative to the surface of the sample. Deflections of the cantilever, or changes in its oscillation, which are detected while rastering correspond to topographical (or other) features of the sample. Deflections or changes in oscillation are typically detected by an optical lever arrangement whereby a light beam is directed onto a cantilever in the same reference frame as the optical lever. The beam reflected from the cantilever is made to illuminate a position sensitive detector (PSD). As the deflection or oscillation of the cantilever changes, the position of the reflected spot on the PSD changes, causing a change in the output from the PSD. Changes in the deflection or oscillation of the cantilever are typically made to trigger a change in the vertical position of the cantilever base relative to the sample, in order to maintain the deflection or oscillation at a constant pre-set value. It is this feedback that generates an AFM image. AFMs can be operated in a number of different imaging modes, including contact mode where the tip of the cantilever is in constant contact with the sample surface, and oscillatory modes where the tip makes no contact or only intermittent contact with the surface.

Actuators are commonly used in AFMs, for example to raster the probe relative to the sample surface or to change the position of the cantilever base relative to the sample surface. The purpose of actuators is to provide relative movement between the probe and the sample. For different purposes and different results, it may be useful to actuate the sample, or the tip or some combination of both. Sensors are also commonly used in AFMs. They are used to detect movement of various components of the AFM, including movement created by actuators. For the purposes of the specification, unless otherwise specified, the term "actuator" refers to a broad array of devices that convert input signals into physical motion, including piezo activated flexures, piezo tubes, piezo stacks, blocks, bimorphs, unimorphs, linear motors, electrostrictive actuators, electrostatic motors, capacitive motors, voice coil actuators and magnetostrictive actuators, and the term "position sensor" or "sensor" refers to a device that converts a displacement, velocity or acceleration into an electrical signal, including capacitive sensors, inductive sensors (including eddy current sensors), differential transformers (such as described in co-pending applications US20020175677A1 and US20040075428A1, Linear Variable Differential Transformers for High Precision Position Measurements, and US20040056653A1, Linear Variable Differential Transformer with Digital Electronics, which are hereby incorporated by reference in their entirety), variable inductance, optical interferometry, optical deflection detectors (including those referred to above as a PSD and those described in co-pending applications US20030209060A1 and US20040079142A1, Apparatus and Method for Isolating and Measuring Movement in Metrology Apparatus, which are hereby incorporated by reference in their entirety), strain gages, piezo sensors, magnetostrictive and electrostrictive sensors.

SUMMARY OF THE INVENTION

We have developed a nanoindenter that produces very accurate, quantitative characterization for a wide spectrum of materials. The new nanoindenter may be implemented on an atomic force microscope (AFM) platform, but unlike indentation that might be effected with an AFM cantilever, the invention drives the indenting tip perpendicularly into the sample. Displacement and force are measured with optimized LVDT sensors and an Optical Lever, respectively, the same devices that eliminate inaccuracies (e.g. non linearity) present in measurements made with AFMs, and this greatly increases sensitivity and resolution in comparison to commercial indenters. This highly quantitative tool, incorporating high end AFM capabilities breaks new ground in characterization of a great diversity of materials including thin films, coatings, polymers, etc. As noted, the nanoindenter may be implemented on an AFM platform and when integrated with the native metrology abilities of the Molecular Force Probe-3D AFM of Asylum Research Corporation, it enables the user to perform quantitative indentation measurements and to make quantitative statements regarding the indenter tip shape and indentation volumes and profiles, all with the same instrument set-up.

In addition to an AFM platform, the new nanoindenter may be implemented on other cantilever-based instruments. Cantilever-based instruments include such instruments as AFMs, molecular force probe instruments (1D or 3D), high-resolution profilometers and chemical or biological sensing probes. For the sake of convenience, the specification focuses on AFMs. However, it should be understood that problems addressed and solutions presented by the present invention are also applicable to other instruments with nanoscale motion and metrology applications.

The systems and techniques described herein provide a novel device for nanoscale metrology that permits quantitative measurements of indentation and related parameters better than is presently possible with commercially available tools.

Specifics of the invention will be described in greater detail below.

BRIEF DESCRIPTION OF THE DRAWINGS

FIG. 10 through FIG. 15 are plan views of planar leaf springs of other assembled flexures for other indenter modules.

DETAILED DESCRIPTION

Figure 1A:
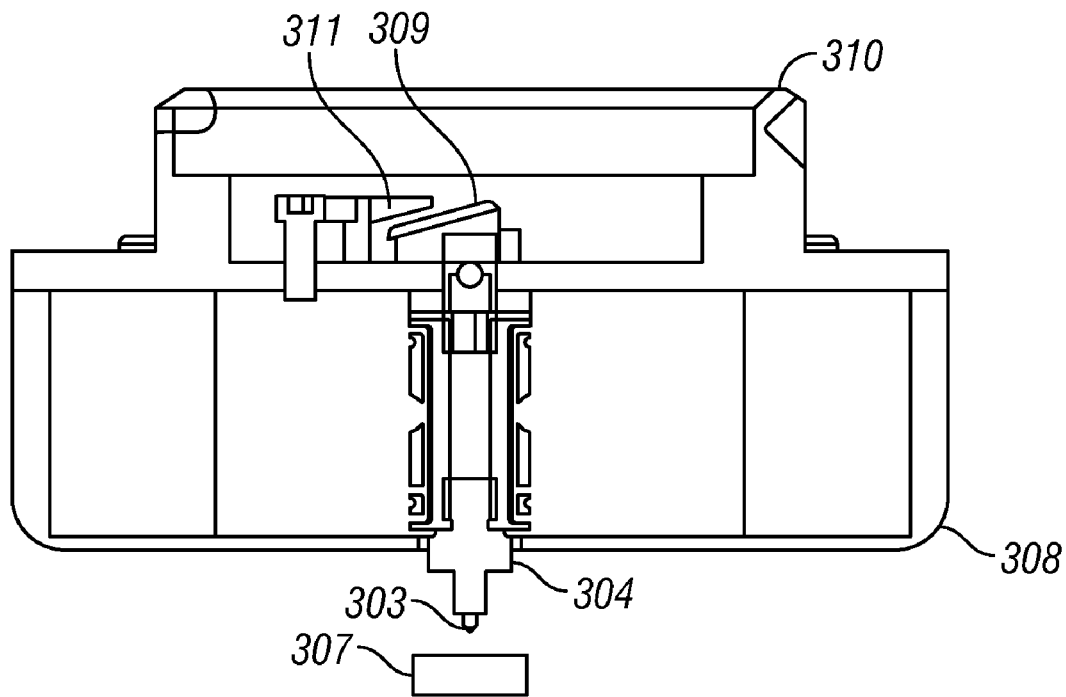
FIG. 1 is the new indenter module attached to an existing AFM.
Figure 1B:
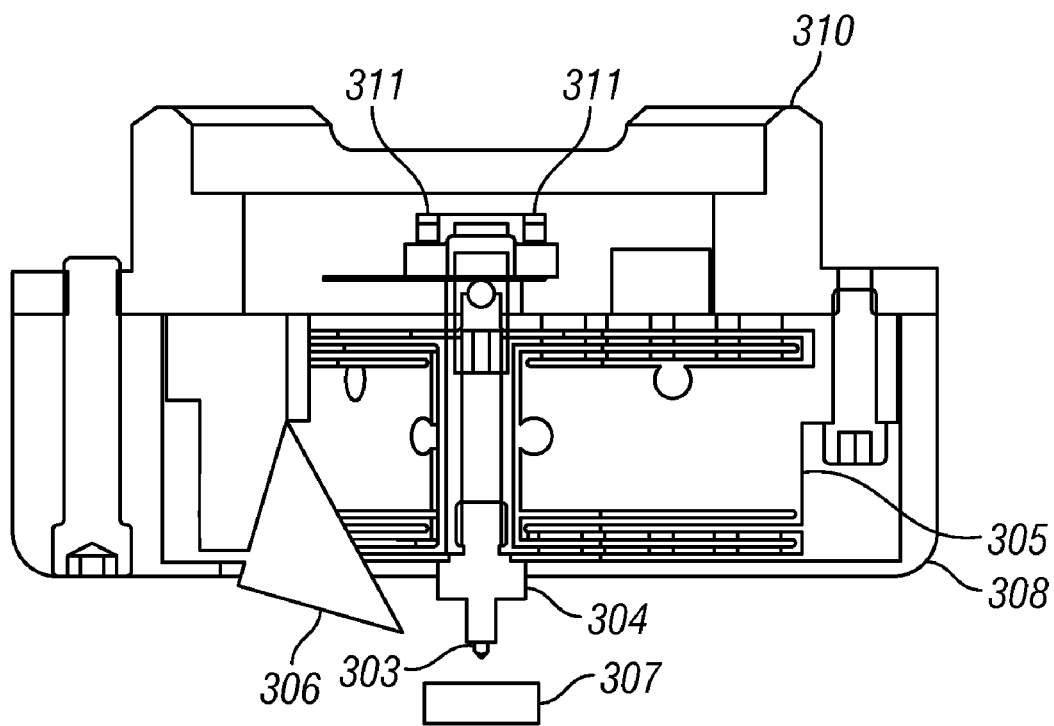

One preferred embodiment of the current invention is depicted in FIG. 1, showing a cross-sectional view of a module embodying the invention which is installed in an AFM in place of the cantilever holder. Panels (A) and (B) of FIG. 1 each show the module rotated 90 degrees about the vertical central shaft of the module which culminates in the indenter probe 303 positioned over a stage 307 on which a sample could be attached. This embodiment of the invention allows it to take direct advantage of some or all of the existing sensors and structures of an AFM.

Figure 2:
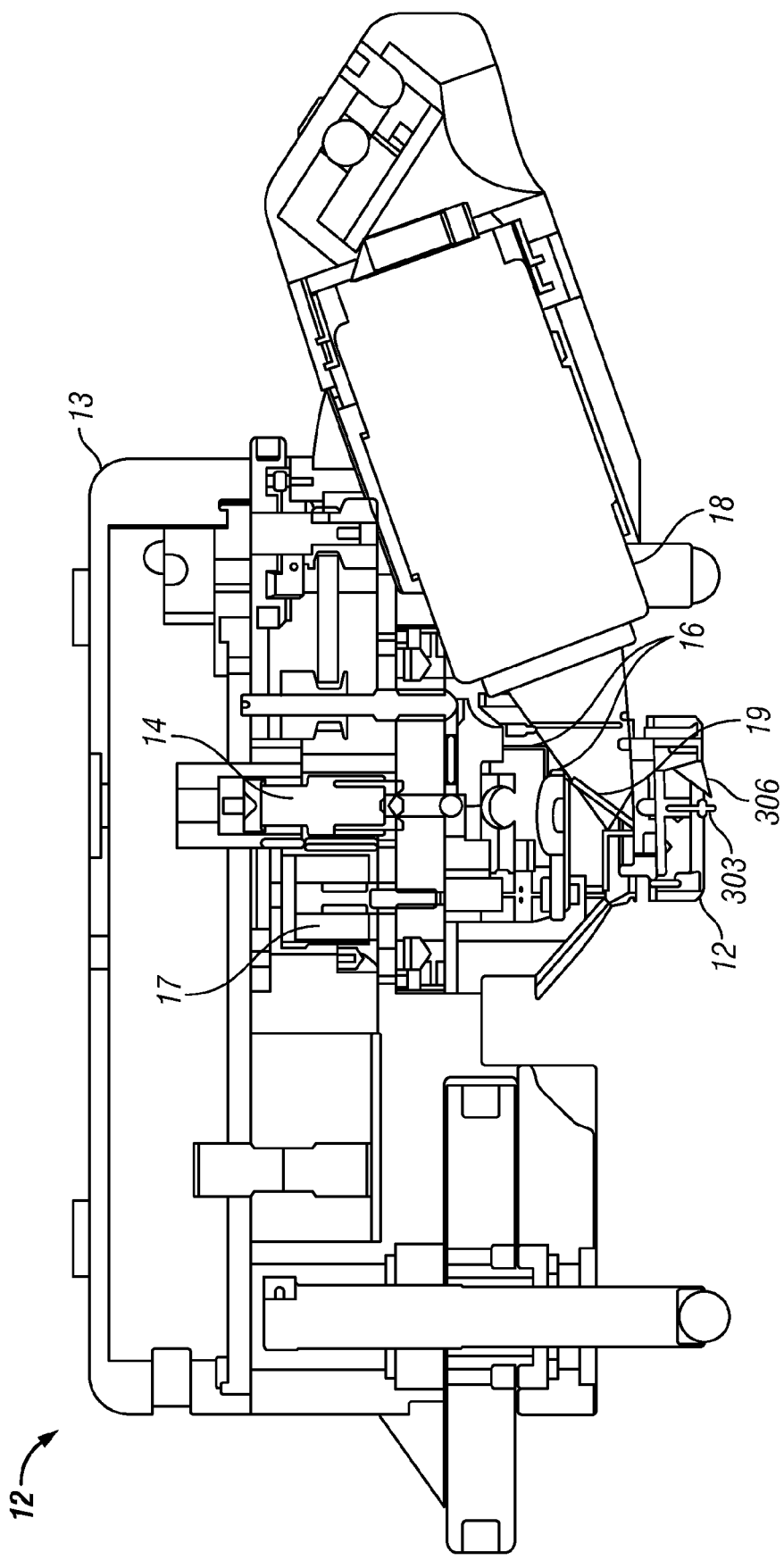
FIG. 2 is the new indenter module placed in the MFP-3D AFM of Asylum Research Corporation.

FIG. 2 shows the module embodying the invention 12 installed in a Molecular Force Probe-3D AFM from Asylum Research Corporation (only the head 13 of the MFP-3D is shown). In the configuration depicted in FIG. 2, the indenter module 12 is removable and make use of the actuators, sensors and optics of the head 13, In particular, the z-piezo 14 of the MFP-3D is used to actuate the indenter probe 303 and the z-LVDT sensor 17 of the MFP-3D may be used to measure the displacement of the indenter probe 303. The position sensitive detector 16 of the MFP-3D is used to measure the motion of the flexure controlling the displacement of the indenter probe 303. Using data from these sensors, it is possible to quantify the displacement and force acting between the indenter probe 303 and a sample (not shown).

Another useful feature of the indenter module 12 being installed in the MFP-3D head 13 is that the module can use certain optical features of the head for providing an optical view of the indenter probe 303 and the sample. The top-view objective 18 and steering mirror 19 of the MFP-3D head 13 work with the prism of the indenter module 12 to provide an optical view of both the indenter probe 303 and the sample (not shown), as well as to illuminate both. This is of great utility for aligning the indenter probe 303 with particular structures on the sample.

The indenter can similarly be installed in AFMs manufactured by other companies and, with modifications, in yet other AFMs. The MFP-3D of Asylum Research Corporation is particularly amenable to conversion to an indenter because the actuators, sensors and optics located in its head are appropriate and convenient for indenter purposes. The same is true of other AFMs, or could be made to be true with modifications.

Except where clearly stated otherwise, the remainder of this Detailed Discussion of the current invention is directed at an indenter module that might be installed in any AFM, not just the MFP-3D of Asylum Research Corporation, as well as to a stand-alone indenter that is not a component of an AFM.

Figure 3:
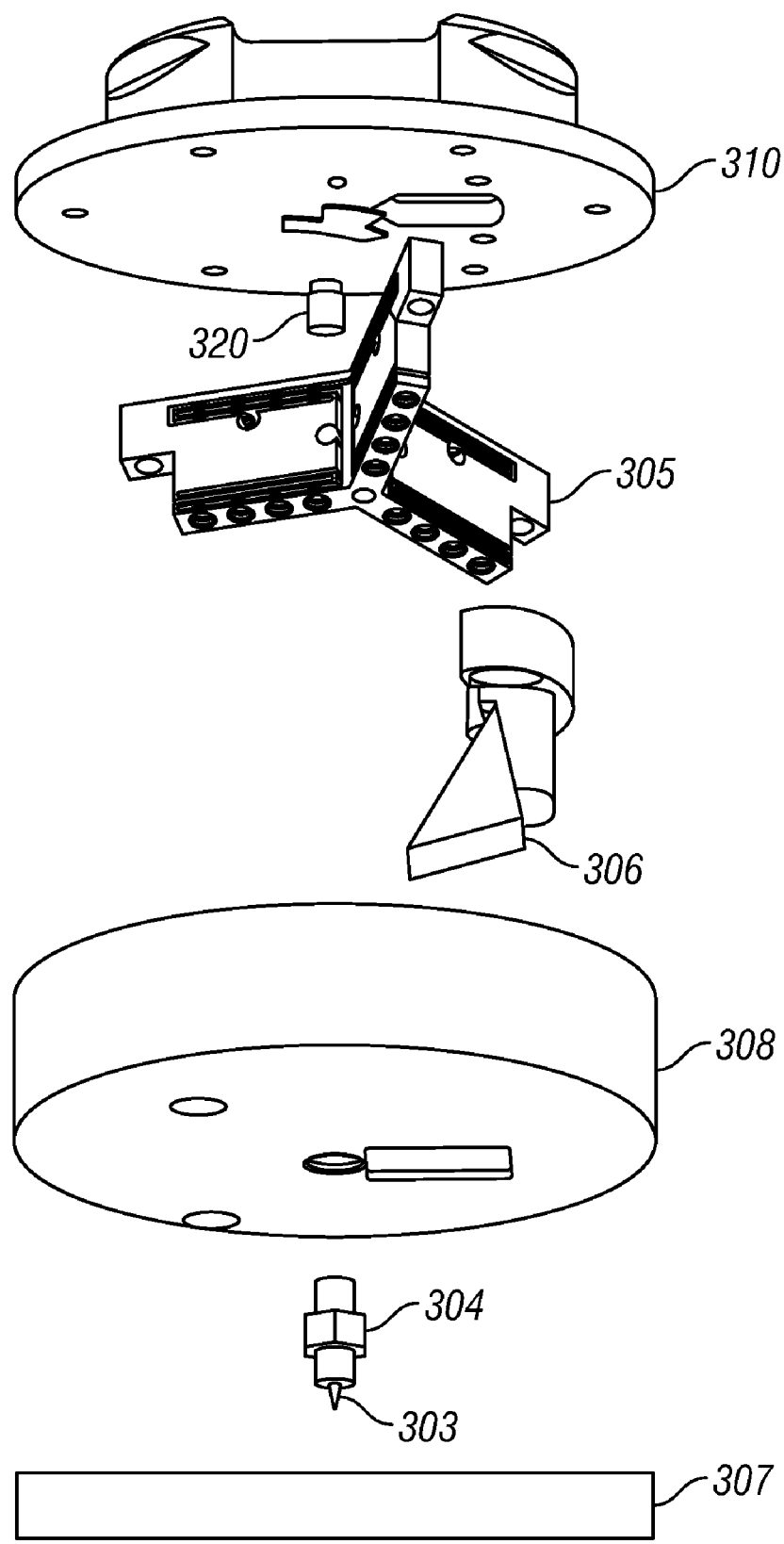
FIG. 3 is the new indenter module prior to assembly.

FIG. 3 shows a perspective view of the module embodying the invention prior to assembly. The indenter probe 303 is mounted on a removable chuck 304. The chuck 304 allows the user to employ a variety of standard and custom indenter probes and to change easily from one probe to another. As is well-known to those versed in the art, these probes are formed of different materials, including diamond, tungsten, silicon nitride and others. The chuck 304 is attached to a monolithic three-dimensional leaf spring flexure 305 which is designed to constrain the motion of the indenter probe 303 to the z-axis only, that is, perpendicular to the sample. Precluding motion in the other axes is a major contributor to the results available with the invention. The flexure 305 is rigidly attached to the bottom of a circular plate with a retaining ring 310 on its top which is designed to mount into an AFM in place of the cantilever holder. This permits the actuator (not shown), which in an AFM would be used to change the position of the cantilever base in response to changes in the deflection or oscillation of the cantilever, to be used to actuate the circular plate/retaining ring 310 and through it to actuate the flexure 305, the chuck 304 and the indenter probe 303. Measurement of this actuation may be improved through the use of a sensor (not shown) to measure the displacement.

As shown in FIG. 3, the module embodying the invention may also include a prism 306 to permit an oblique view of the sample (not shown) on the sample holder 307, the indenter probe 303 and their interface where the AFM in which the module is mounted includes an optical view system. The module may also include a dust cover 308 to protect the flexure 305, the circular plate/retaining ring 310 and the prism 306 from external contamination and prevent damage from handling. The dust cover 308 may also provide mechanical hard stops (not shown) to prevent the flexure 305 from being overextended. A shake piezo (not shown) to oscillate the flexure 305, and thus the chuck 304 and the indenter probe 303, when the measurement is to be made in an AC mode could be added at the point where collar 320 screws into the flexure 305 or alternatively could be attached to the circular plate/retaining ring 310.

Figure 4:
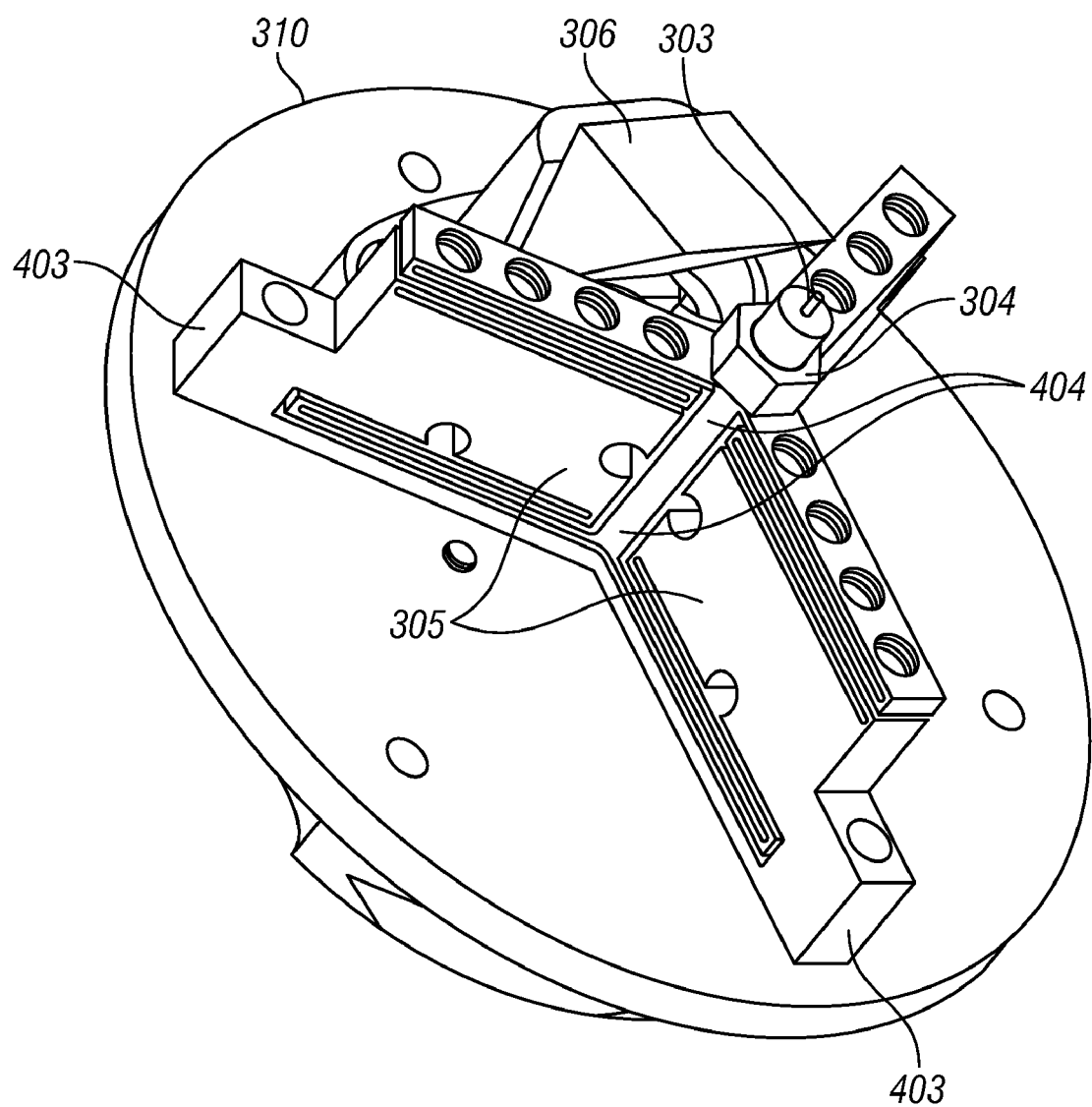
FIG. 4 is the flexure mounted on the circular plate/retaining ring of the new indenter module.

FIG. 4 is a perspective view of the flexure 305 mounted on the circular plate/retaining ring 310, with the chuck 304, the indenter probe 303 and the prism 306 shown assembled. The flexure 305 is a monolithic, three-dimensional leaf spring with three supporting ends 403 and a flexing portion, the central shaft 404, which is free to move in response to the application of force. The supporting ends 403 are each rigidly attached to the circular plate/retaining ring 310. The chuck 304 is rigidly attached to one end of the flexing portion, the central shaft 404, and the indenter probe 303 is attached to the chuck 304, facing the sample to be indented.

Figure 5:
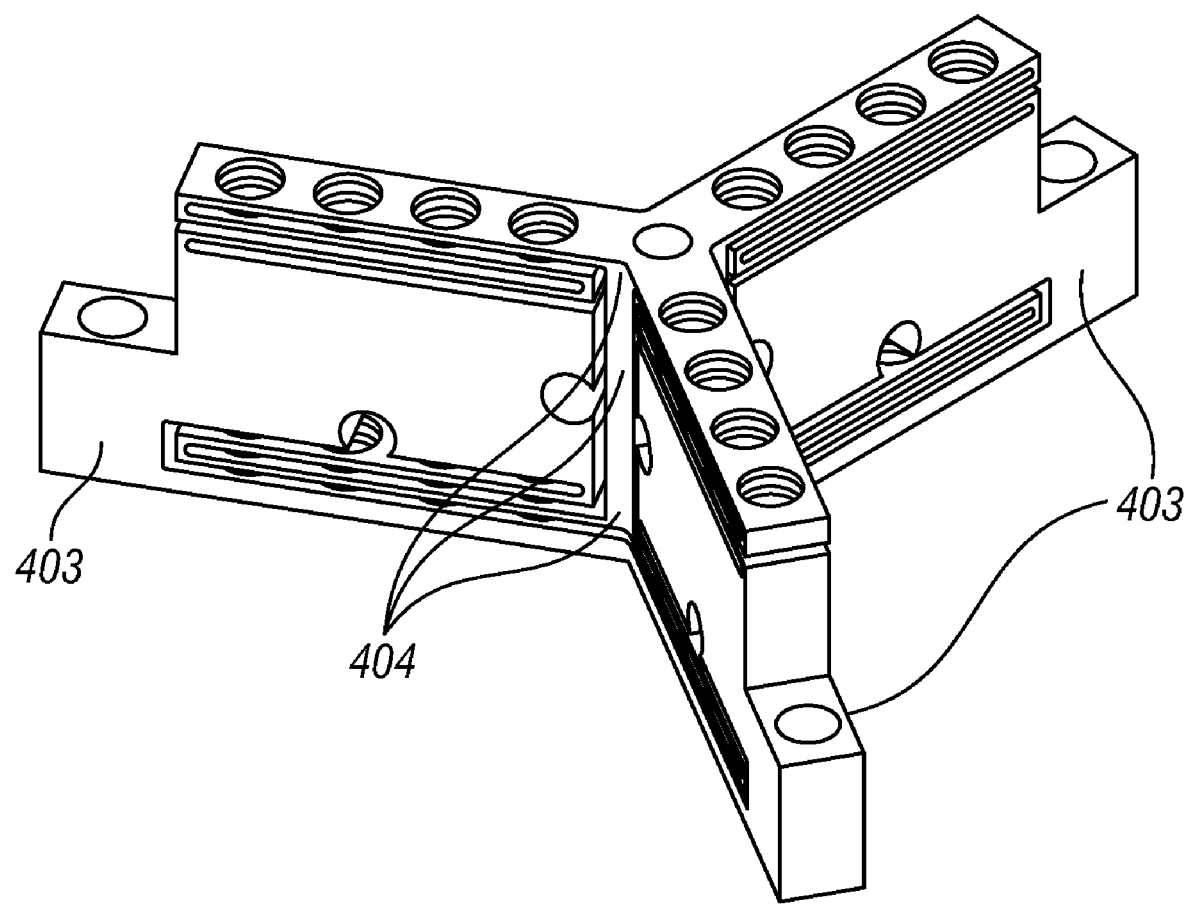
FIG. 5 is the flexure of the new indenter module.

FIG. 5 is a second perspective view of the flexure 305, absent the other items shown in FIG. 4. Such flexures are fabricated using metals and machining methods, including electronic discharge machining, well-known to those versed in the art.

Figure 6:
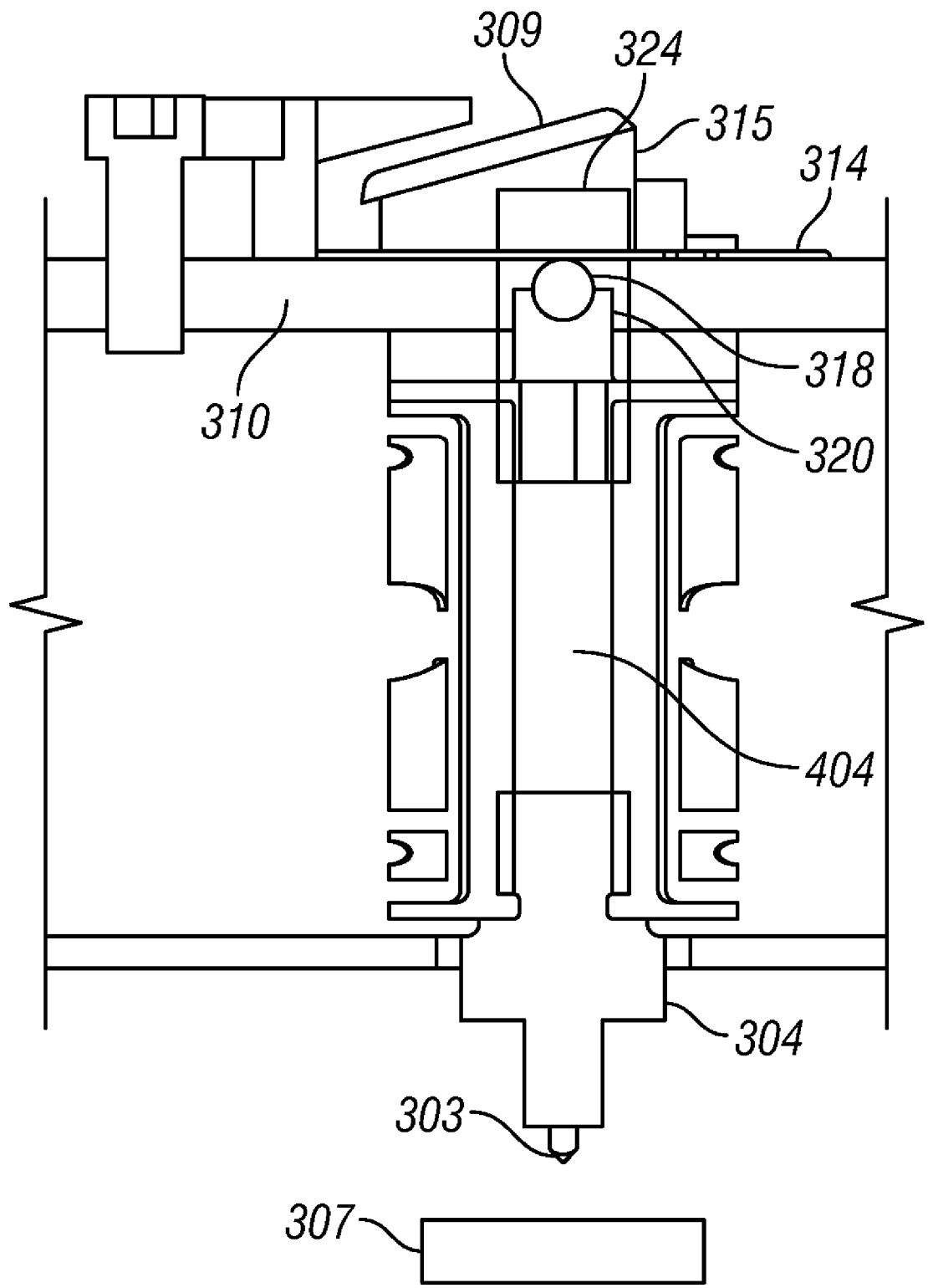
FIG. 6 is a cross sectional view of the mechanical converter system of the new indenter module.

FIG. 6 shows a cross-sectional view of the central shaft 404 of the flexure 305, with the chuck 304 attached to one end (and the indenter probe 303 attached to the chuck 304) and a collar 320 attached to the other end which is inserted through a hole in the center of the circular plate/retaining ring 310 and gives access to the central shaft 404 from within the AFM to enable a mechanical converter assembly. The purpose of the mechanical converter assembly is to convert the z-axis linear motion of the central shaft 404, chuck 304 and indenter probe 303 into an angular change that an optical lever detector system, which in an AFM would be used to detect changes in the deflection or oscillation of the cantilever, can measure. When the indenter module is mounted into an AFM in place of the cantilever holder and the circular plate/retaining ring 310 is actuated, thereby displacing flexure 305, chuck 304 and indenter probe 303 toward the sample, one end of a second flexure, planar flexure 314, which is rigidly attached to the circular plate/retaining ring 310 is also displaced. At the same time, the other end of planar flexure 314, which on one side is linked though a ball bearing mechanism 318 to the central shaft 404 and on the other side is attached to a wedge-shaped mirror mount 315, and is free to flex is also displace, with the displacement following that of the central shaft 404. This displacement of the flexing end of the planar flexure 314 tilts the mirror mount 315, and mirror 309 attached to the mount, and thereby steers the light beam of an optical lever detection system (not shown) from one place on the position sensitive detector of the system to another thereby providing a measure of the displacement of the indenter probe 303. A small permanent magnet 324 keeps the mirror mount 315 and planar flexure 314 in contact with the ball bearing surface 318.

The design of the mechanical converter assembly allows the motion of the indenter tip 303 to be measured in much the same manner as cantilever tip deflection or oscillation are measured in a conventional AFM. Together with the use of the z-axis actuator previously discussed, this allows the indenter module to be easily swapped with the cantilever holder of an AFM, resulting in a unique, useful and versatile instrument that allows the user to bring the functionality of an AFM to bear on indenting.

Figure 7:
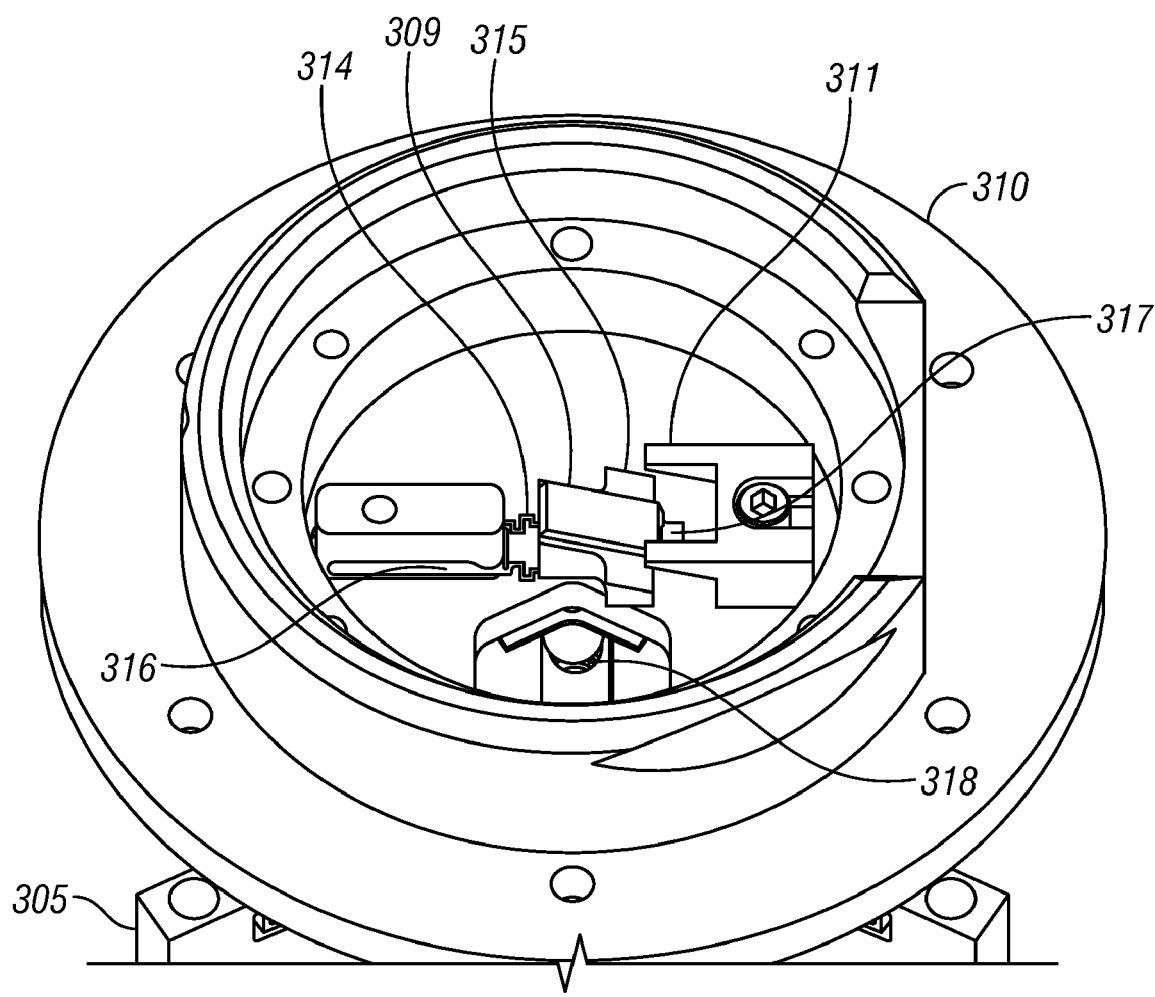
FIG. 7 is a perspective view from the top of the mechanical converter system of the new indenter module.

FIG. 7 shows a perspective view from above of the mechanical converter assembly discussed in the preceding paragraph. The two ends of the planar flexure 314, the support end 316 rigidly attached to the circular plate/retaining ring 310, and therefore displaced in tandem with actuation of the circular plate/retaining ring, 310 and the flexing end 317 linked though a ball bearing mechanism 318 to the central shaft 404 and also attached to the mirror mount 315, and therefore displaced in tandem with the central shaft, are displayed with greater clarity. FIG. 7 also shows the hard stops 311 built into the mechanical converter assembly to prevent the flexure 305 from being overextended or damaged by normal handling.

The planar flexure 314 has a very high compliance when compared to the indenting flexure 305, that is, the spring constant of the planar flexure 314 is very low compared to the spring constant of the indenting flexure 305.

It will be observed that the indenting flexure 305 plays a major role in the performance of the preferred embodiment of the current invention which has just been discussed. A second preferred embodiment, employing a different indenting flexure but, like the first preferred embodiment, designed to be installed in an AFM in place of the cantilever holder in order to make use of the actuators, sensors and optics of the AFM is depicted in FIG. 8, a perspective view of the module embodying the invention prior to assembly.

Figure 8:
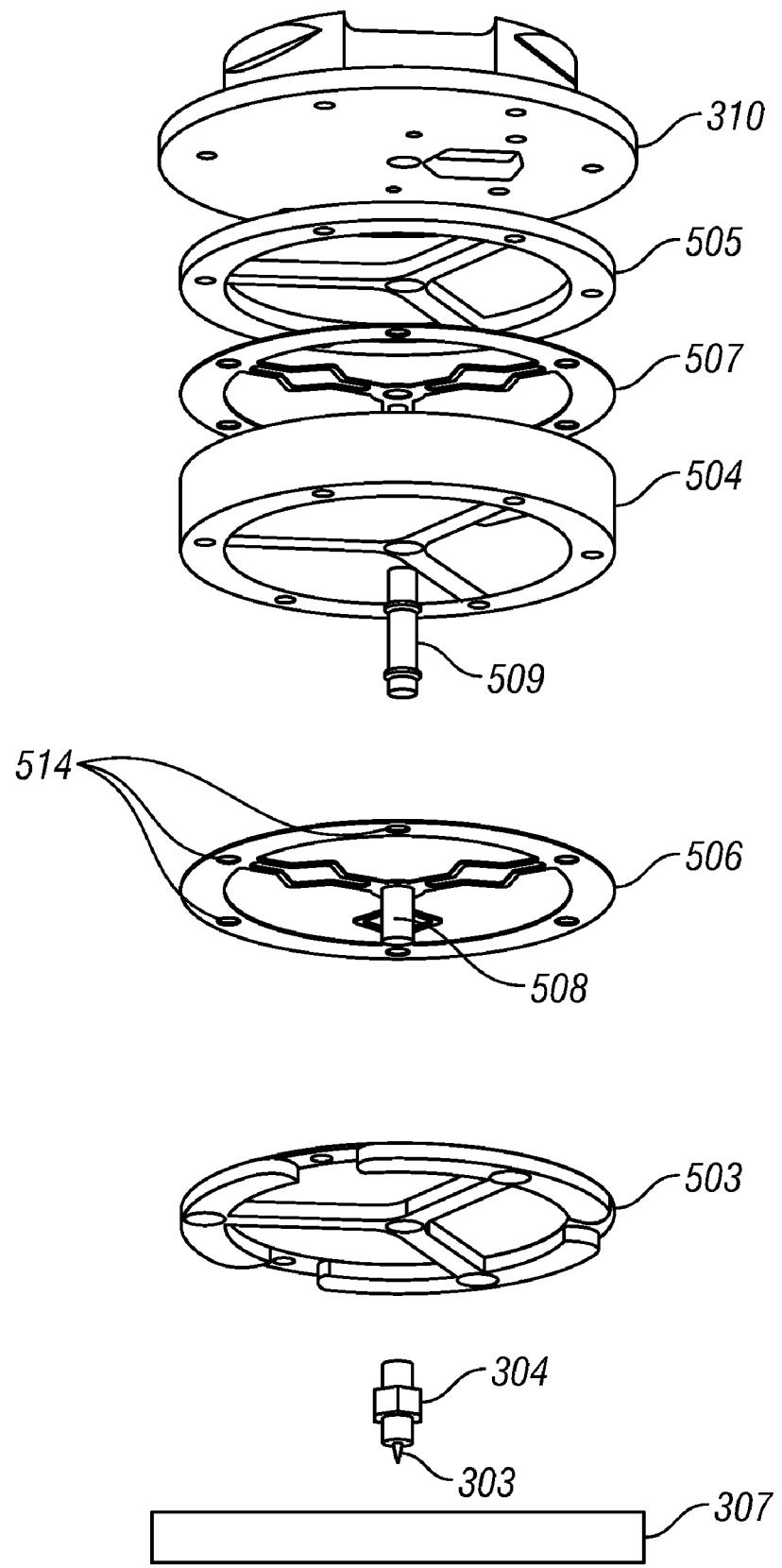
FIG. 8 is another new indenter module prior to assembly.

Unlike the monolithic three-dimensional leaf spring flexure 305 of the first preferred embodiment, the flexure of FIG. 8 is an assembled flexure. Like that flexure, however, the assembled flexure of FIG. 8 is designed to constrain the motion of the indenter probe 303 to the z-axis only, that is, perpendicular to the sample. The flexing portion of the assembled flexure of FIG. 8 is provided by the central shaft of two circular, planar leaf springs 506 and 507, which are firmly constrained at the support end, that is the perimeter, by interleaved clamps, 503, 504 and 505. The assembly of planar leaf springs 506 and 507 and interleaved clamps, 503, 504 and 505 is rigidly attached to the circular plate/retaining ring 310. The central shaft of the planar leaf springs 506 and 507 is composed of spindles 508 and 509. The upper end of spindle 508 screws into the lower end of spindle 509, through holes 514, clamping planar leaf spring 506 against the stop at the lower end of spindle 509. The stop at the upper end of spindle 509 is fastened to planar leaf spring 507 and the portion of the spindle above the stop extends through a hole in the center of the circular plate/retaining ring 310 and gives access to the central shaft from within the AFM to enable the mechanical converter assembly discussed above in connection with the first preferred embodiment to function.

As with the first preferred embodiment, the central shaft of the assembled flexure of FIG. 8 ends with the chuck 304, rigidly attached to the lower end of spindle 508, and the indenter probe 303 attached to the chuck 304, facing the sample to be indented. The assembled flexure, the chuck 304 and the indenter probe 303 are actuated by actuating the circular plate/retaining ring 310 with the actuator (not shown) which in the AFM would be used to change the position of the cantilever base in response to changes in the deflection or oscillation of the cantilever.

Figure 9:
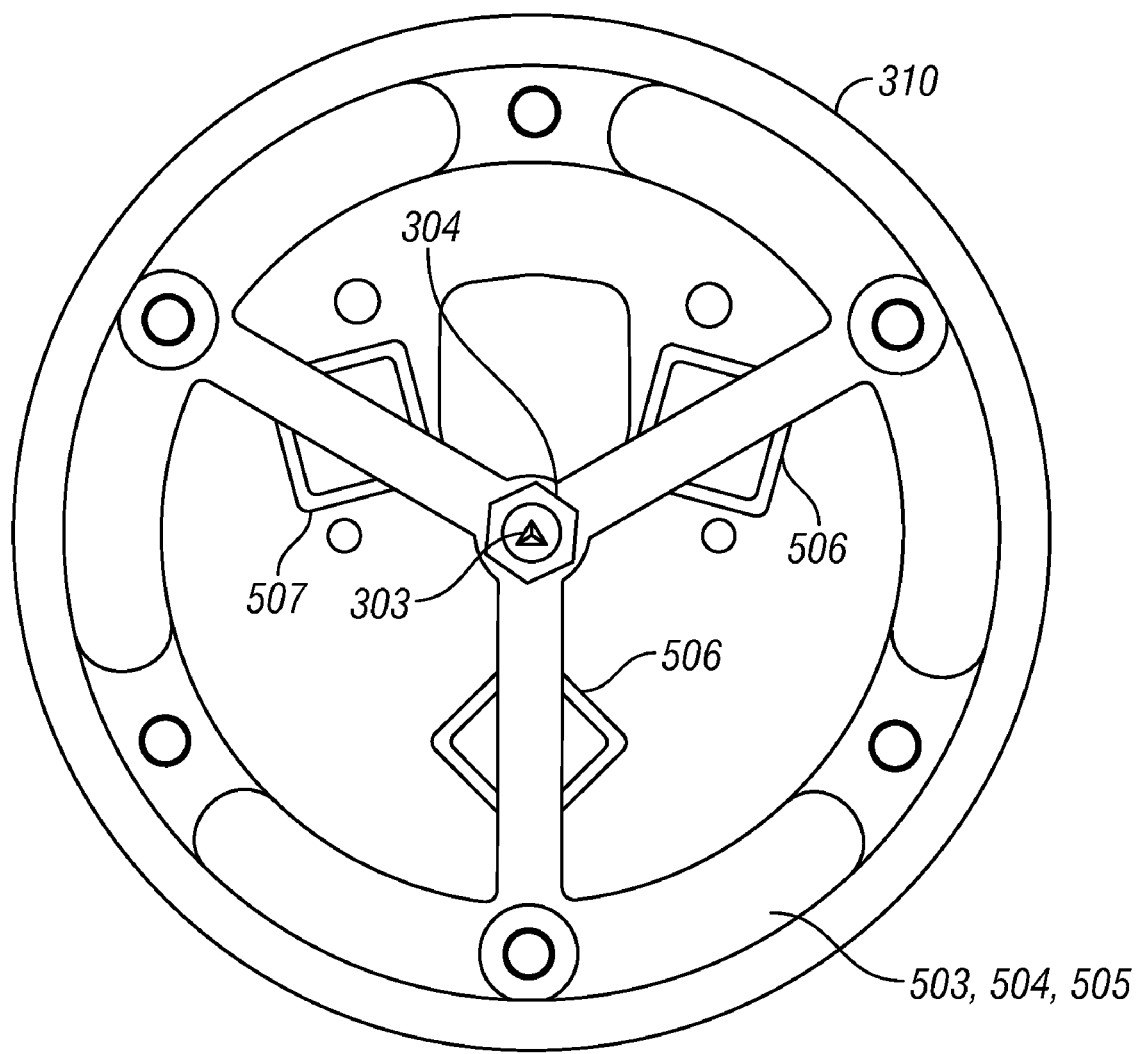
FIG. 9 is a bottom-side plan view of the indenter module of FIG. 8 after assembly.
Figure 10:
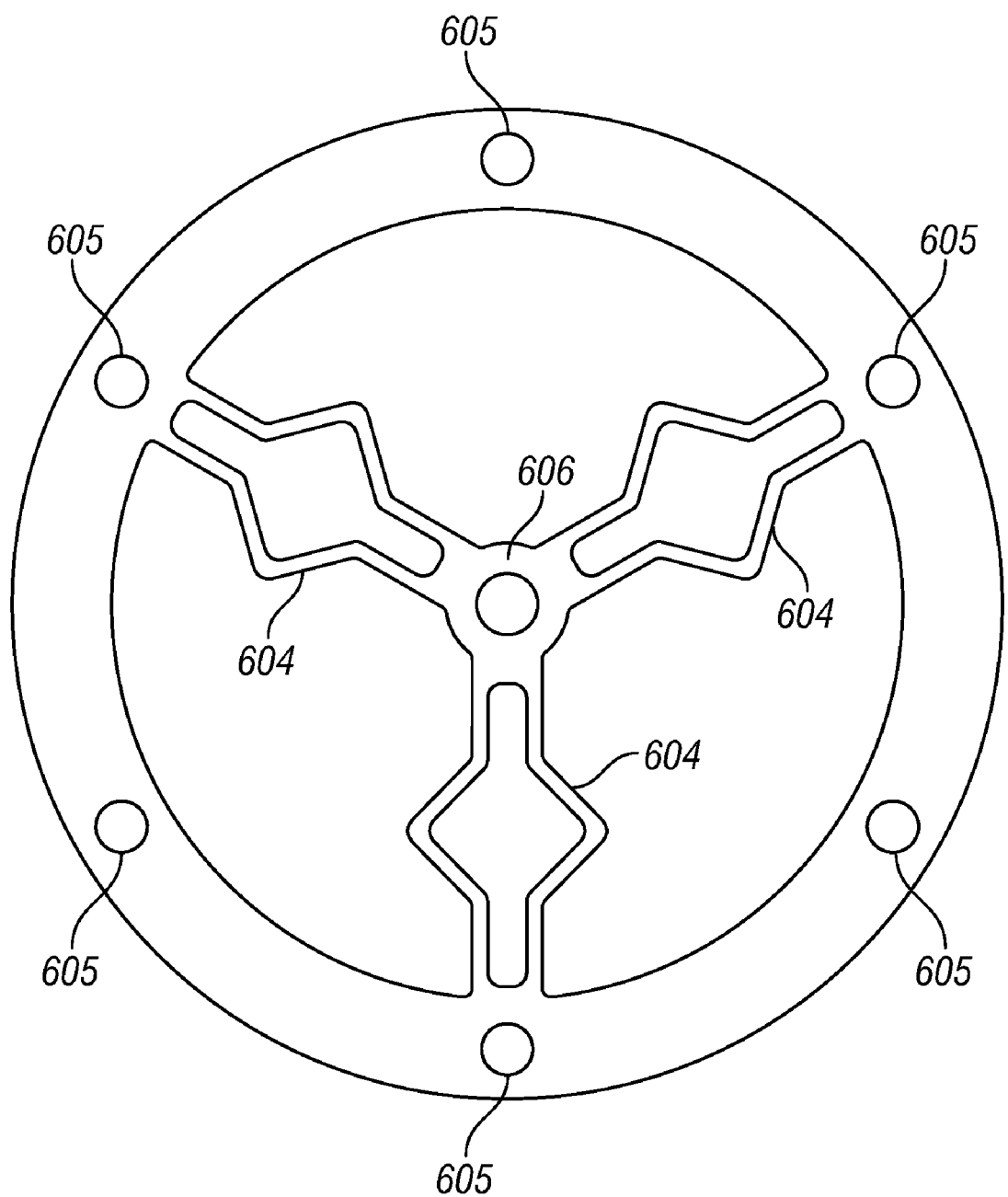
FIG. 10 is a plan view of the planar leaf springs of the assembled flexure of indenter module of FIG. 8.

FIG. 9 is a bottom-side plan view of the flexure of FIG. 8 after assembly. FIG. 10 is a plan view of the planar leaf springs 506 and 507 of the flexure of FIG. 8, showing different parts of the springs. Such springs are fabricated using metals, including beryllium copper, and machining methods well-known to those versed in the art.

Figure 11:
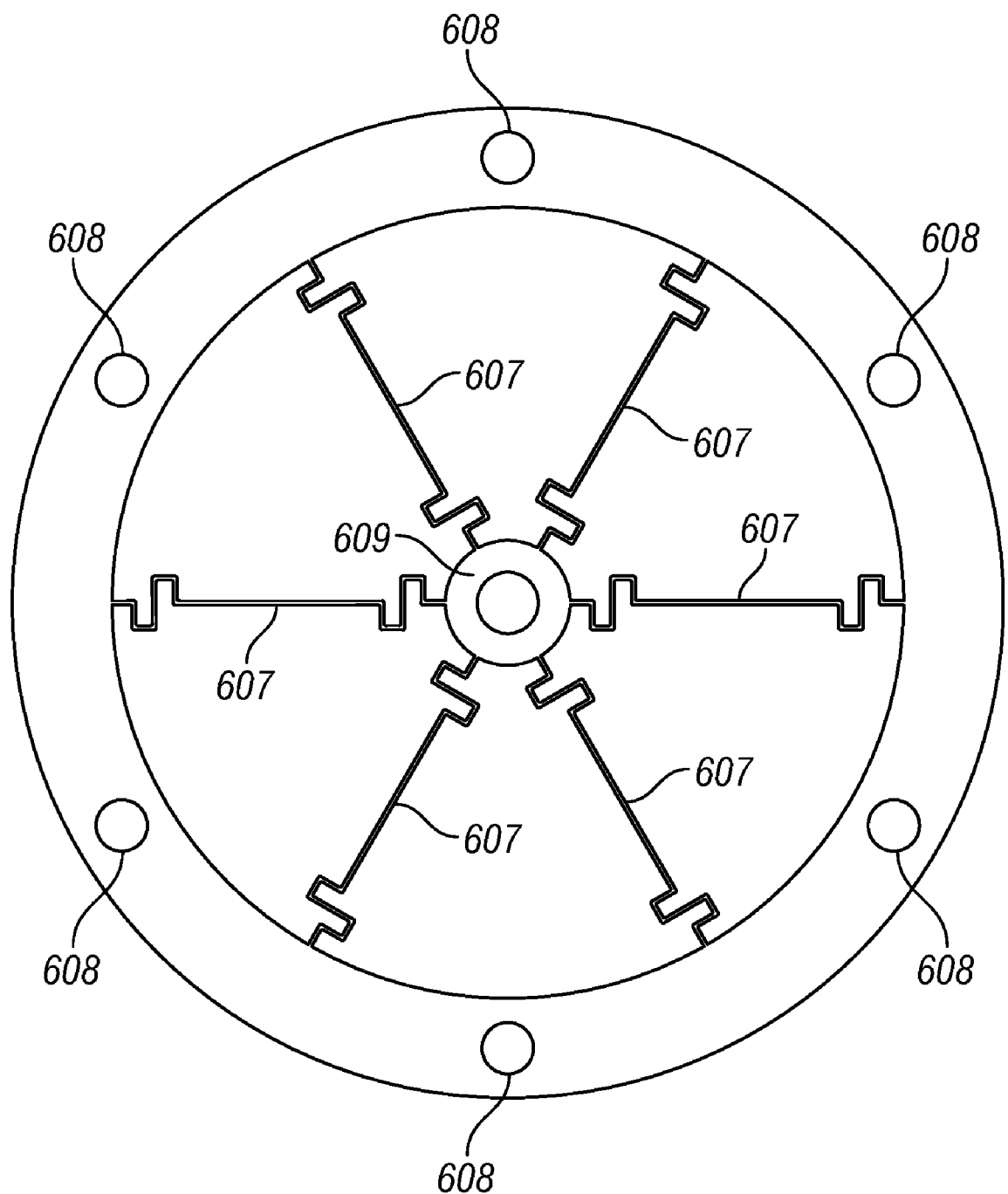
Figure 12:
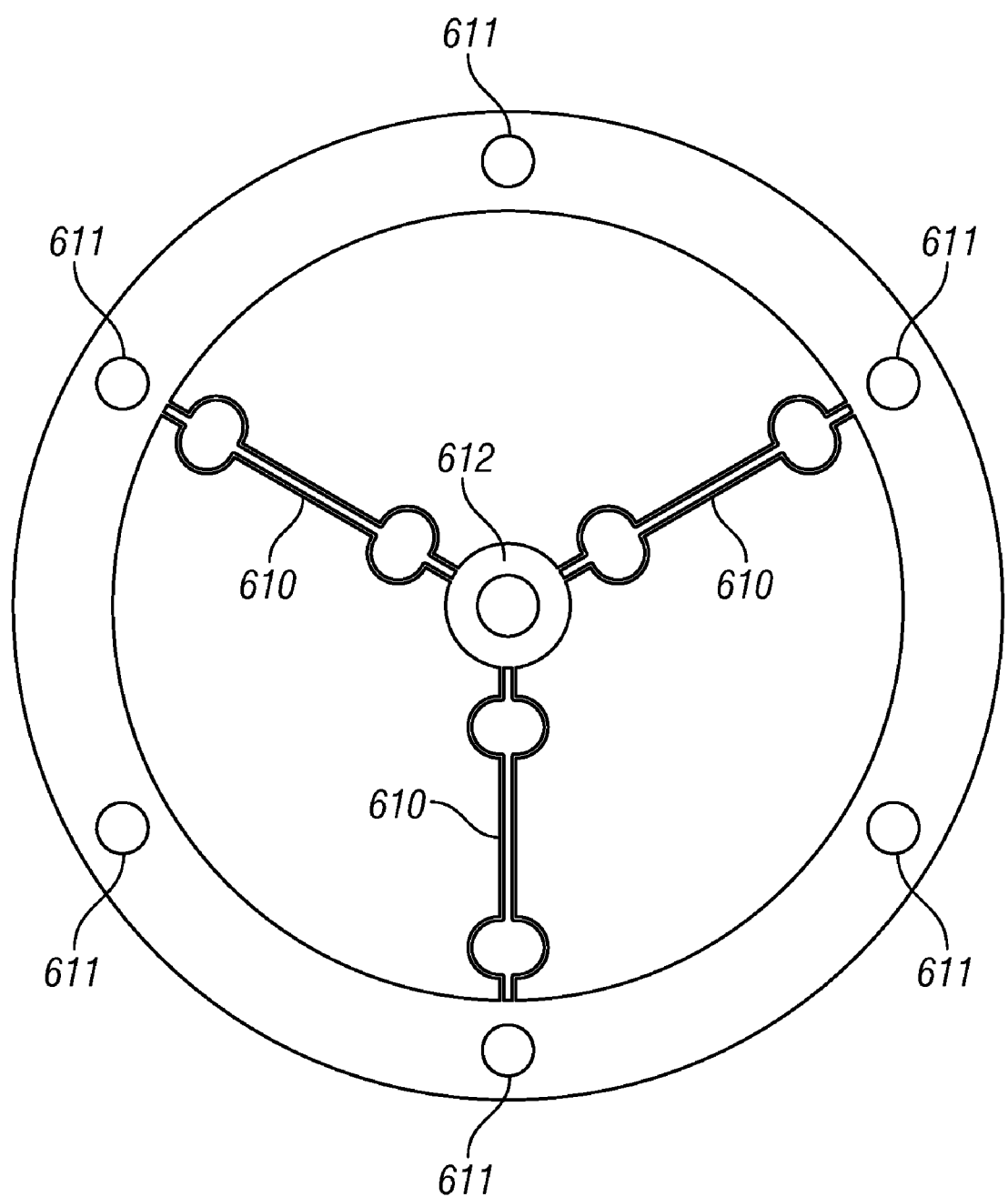
Figure 13:
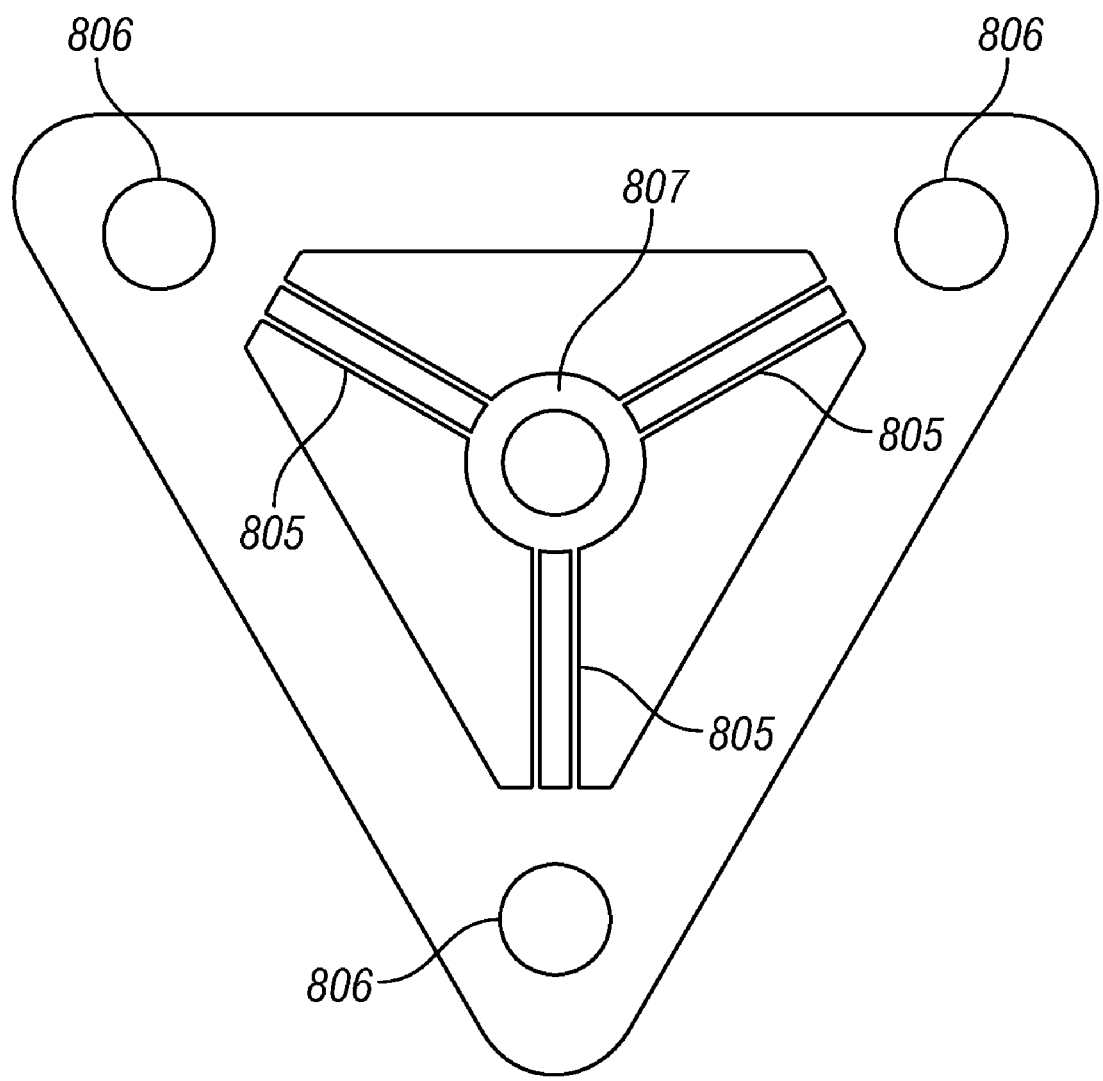
Figure 14:
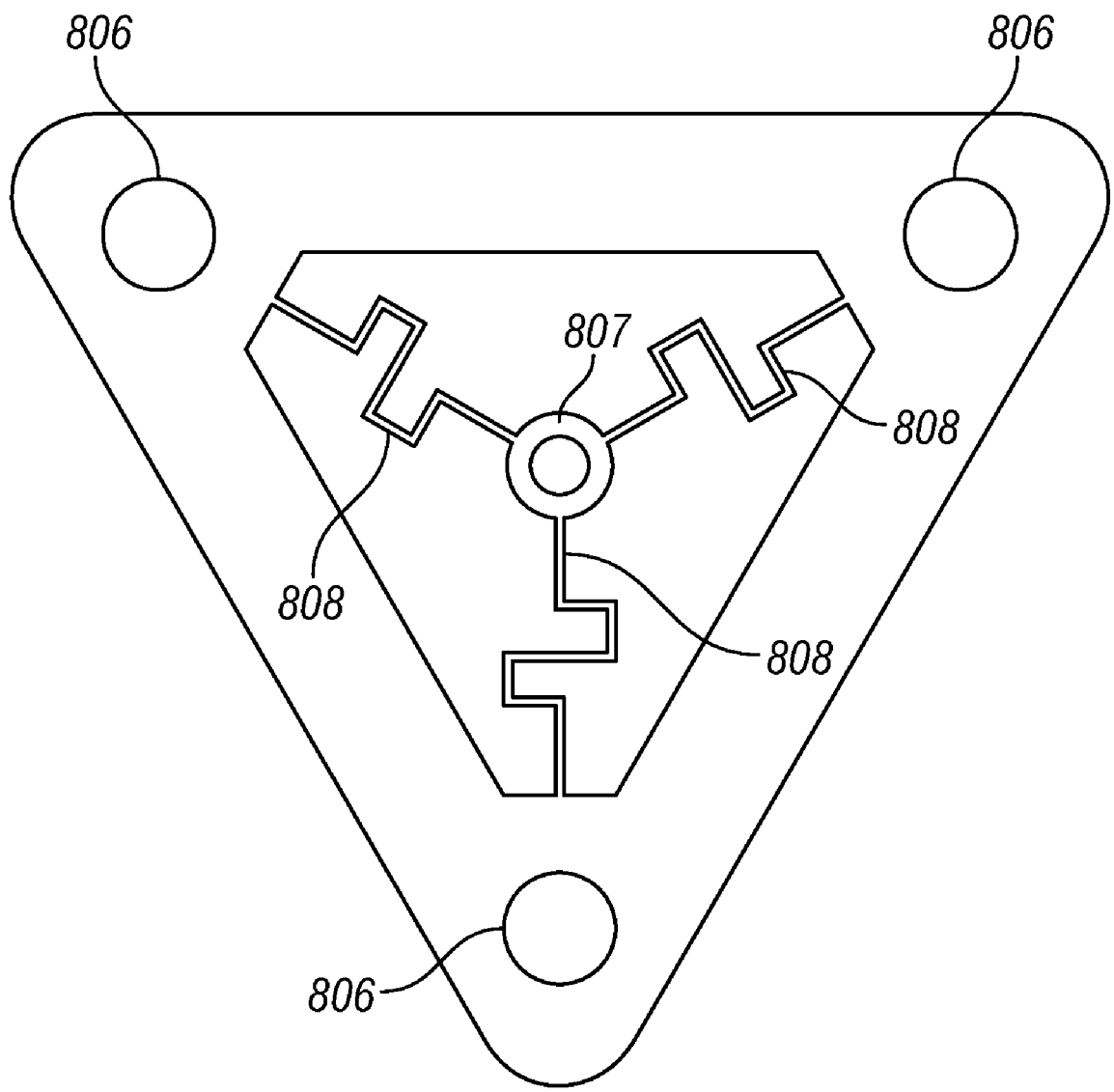
Figure 15:
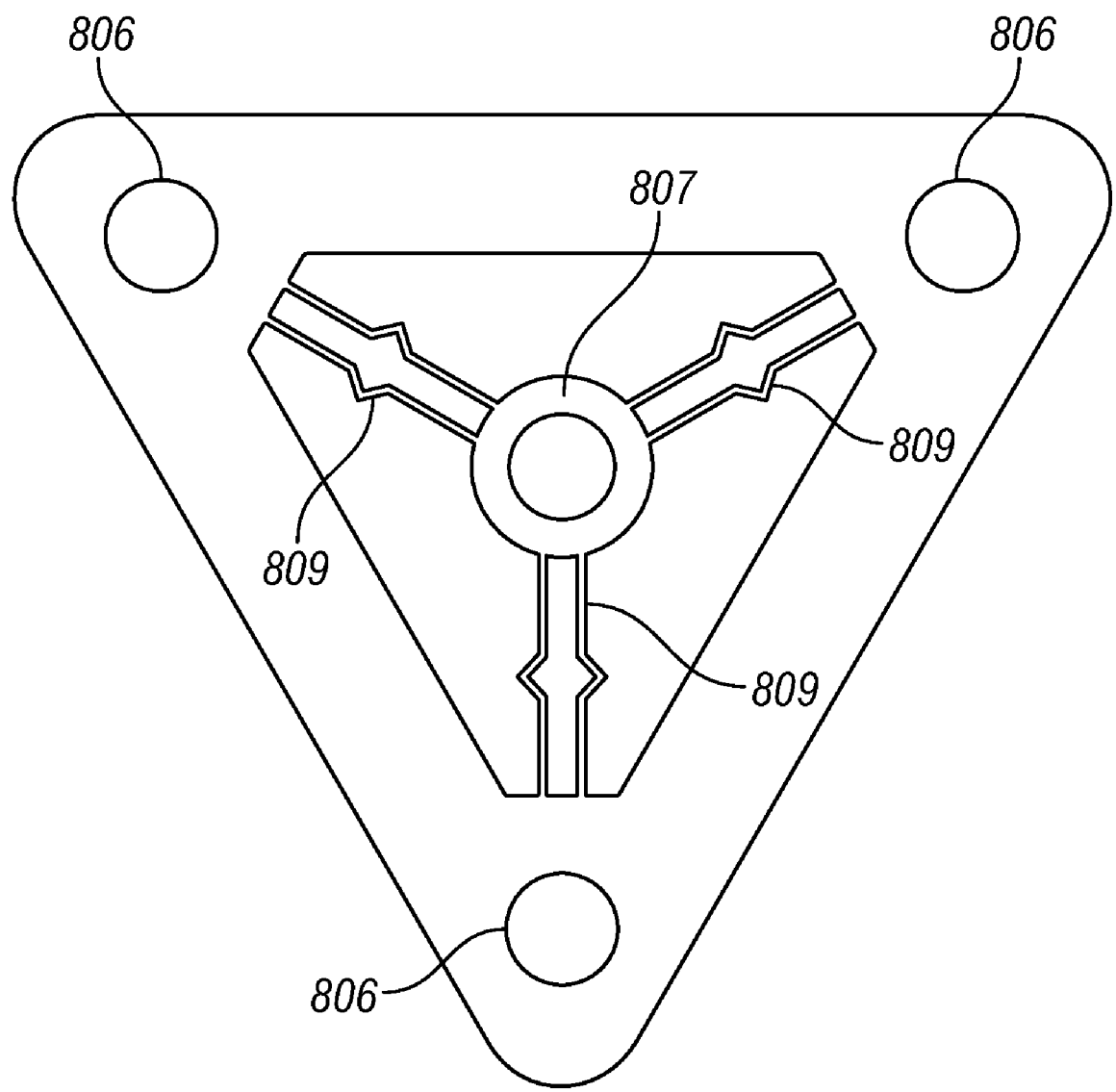
Figure 18:
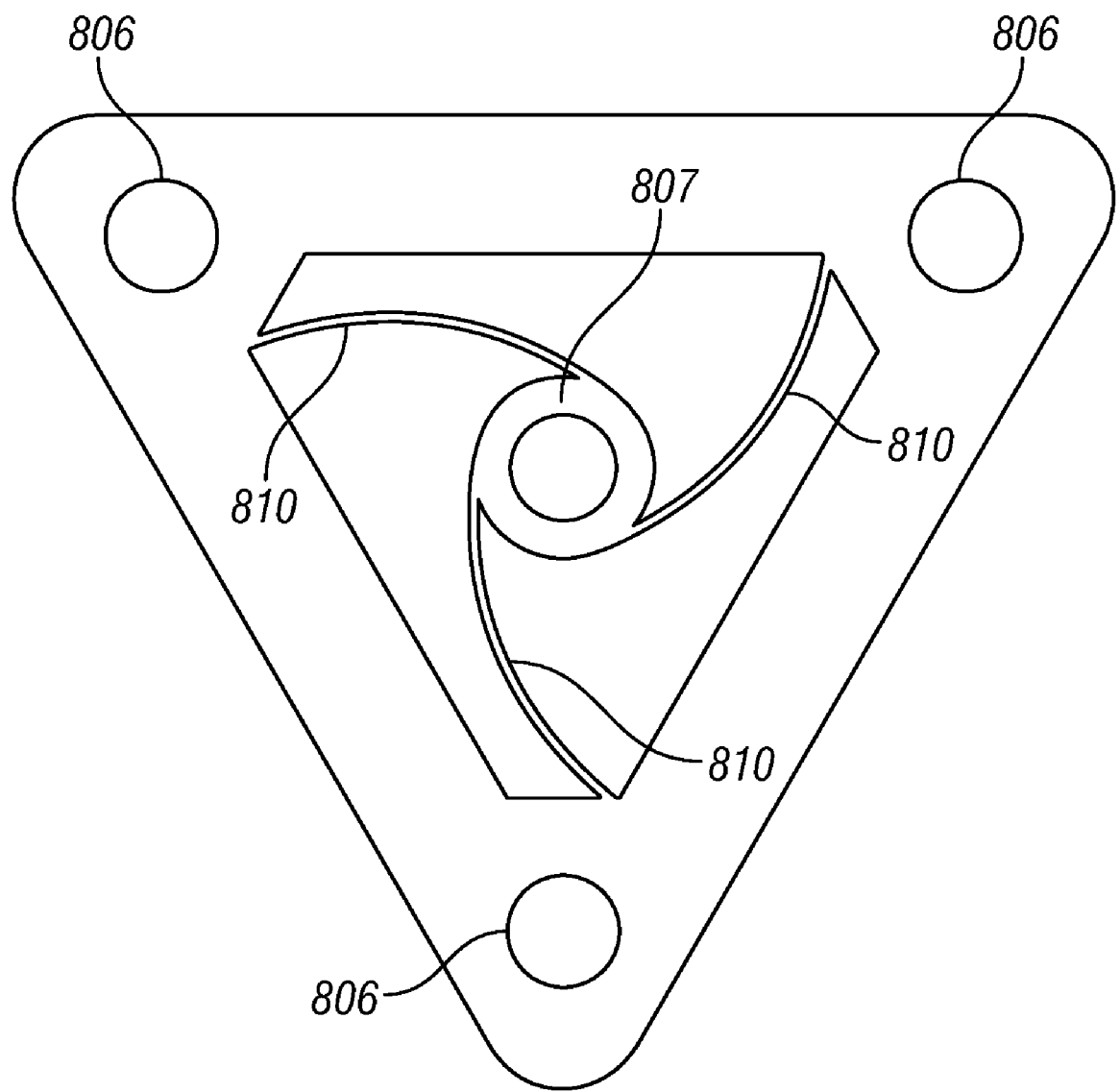
FIG. 18 is a plan view of the planar leaf springs of the assembled flexure of indenter module of FIG. 16.

Other preferred embodiments of the current invention, also designed to be installed in an AFM in place of the cantilever holder in order to make use of the actuators, sensors and optics of the AFM, but employing a different indenting flexures than indenting flexure 305 of the first preferred embodiment or the assembled flexure of FIG. 8, form part of the invention. FIG. 10 shows springs 604, holes 605 and central shaft 606. FIG. 11 shows other springs 607, holes 608 and central shaft 609. FIG. 12 shows other springs 610, holes 611 and central shaft 612. FIG. 13 shows the springs 805, central connection 807 and holes 806. FIG. 14 shows springs 808, central receiving shaft 807 and holes 806. FIG. 15 shows the shaft 807, springs 809 and holes 806. Altogether, FIG. 11 through FIG. 15 are plan views of the planar leaf springs of such other preferred embodiments. Each of them consists of a flexing portion in the center of the spring, support ends at the perimeter and connections from the flexing portions to the support ends of variously shaped beams. In addition to the circles and other depicted shapes of these planar leaf springs, any polygon would in general produce similar results when paired with appropriate connections. Holes 806 and the shaft 807 are also shown in FIGS. 16 and 18 Another embodiment showing springs 810 is also shown in FIG. 18.

Figure 16:
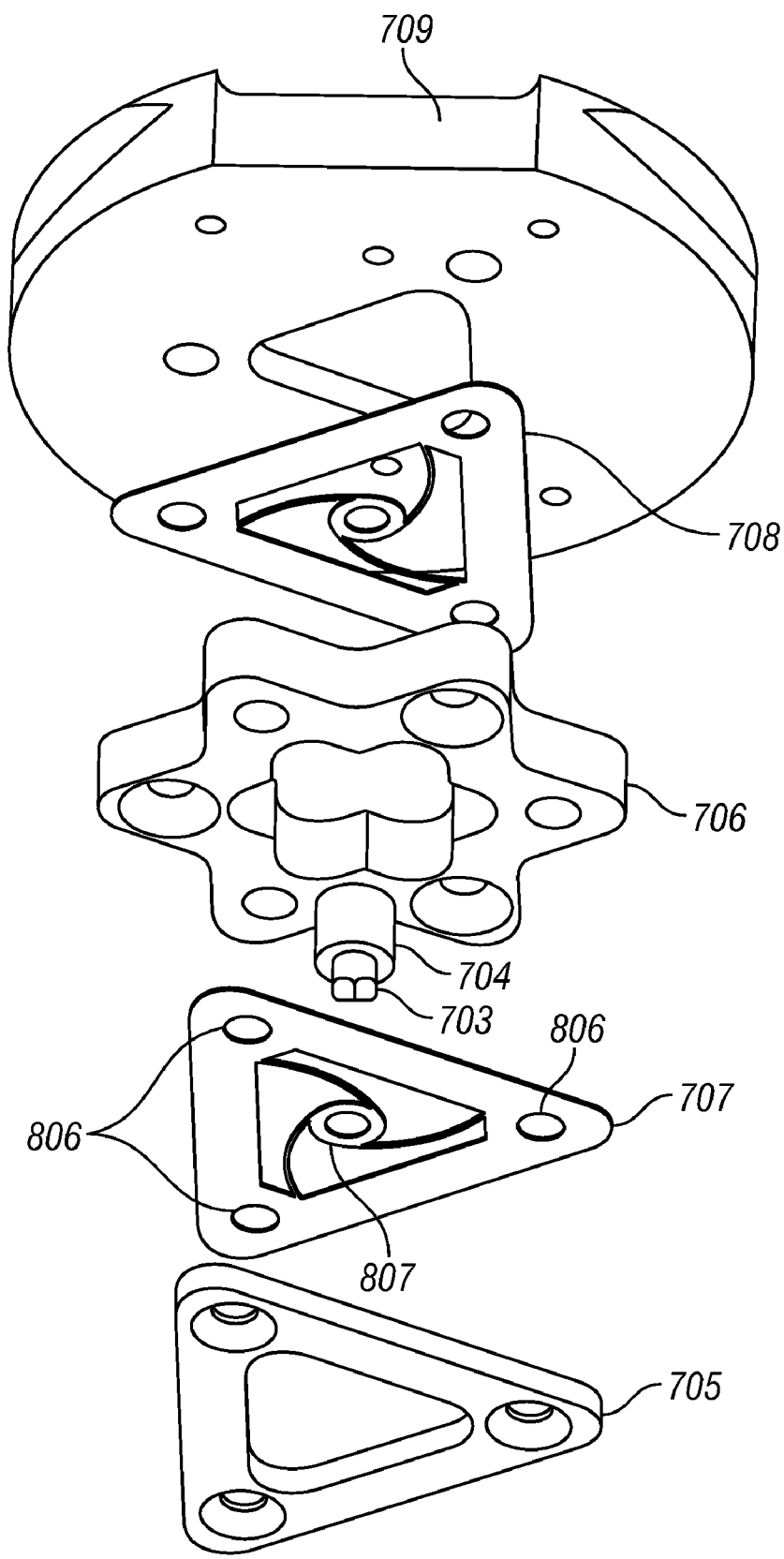
FIG. 16 is another new indenter module prior to assembly.

An additional preferred embodiment, again employing a different indenting flexure but, like the other preferred embodiments disclosed above, designed to be installed in an AFM in place of the cantilever holder in order to make use of the actuators, sensors and optics of the AFM is depicted in FIG. 16, a perspective view of the module embodying the invention prior to assembly. Like the flexure of FIG. 8, the flexure of FIG. 16 is an assembled flexure and is designed to constrain the motion of the corresponding probe 703 (which is also an optical element) to the z-axis only, that is perpendicular to the sample.

The components of the assembled flexure of FIG. 16 are similar to those of the assembled flexure of FIG. 8: two planar leaf springs 707 and 708 separated by clamps 705 and 706. However, the assembled flexure of FIG. 16 does not have a third clamp separating the upper planar leaf spring 708 from the plate 709 which facilitates installation of the assembly in an AFM in place of the cantilever holder. Instead, planar leaf springs 708 is rigidly attached directly to the plate 709.

The central shaft of the planar leaf springs 707 and 708 of the assembled flexure of FIG. 16 also differs from the central shaft of the assembled flexure of FIG. 8. The central shaft of the planar leaf springs 707 and 708 consists of just a chuck 704, and the probe 703 attached to the chuck 704, facing the sample to be indented. The upper end of the chuck 704 extends through a hole in the center of the plate 709 and gives access to the central shaft from within the AFM to enable the mechanical converter assembly discussed above in connection with the first preferred embodiment to function.

The probe 703 of the assembled flexure of FIG. 16 is a new device not currently known in the art and as such is significantly different from the indenter probe 303 of the assembled flexure of FIG. 8. Probe 703 has both a different function than indenter probe 303 and a different construction. Probe 703 has a dual function: it is both an optical element and an indenting probe. As an optical element, probe 703 acts as a lens allowing the optical viewer system of the AFM head in which assembled flexure of FIG. 16 is installed direct optical view of the sample to be indented. As an indenting probe, probe 703 is a rigid element that applies force and indents the sample as with traditional indenter probes, such as 303. With this dual function comes a requirement for a different construction. A probe like probe 703 must be fabricated from a material which is both very hard and transparent to light. Suitable materials include diamond and sapphire.

Probe 703 has many advantages over other indenter transducers or indenting probes. These include making available true top optical view of the sample to be indented, allowing for accurate positioning of indentations and having a combination of low mass and high resonant frequency, which allows unprecedented resolution in the measurement of mechanical behavior of materials through both static and dynamic material testing methods.

Figure 17:
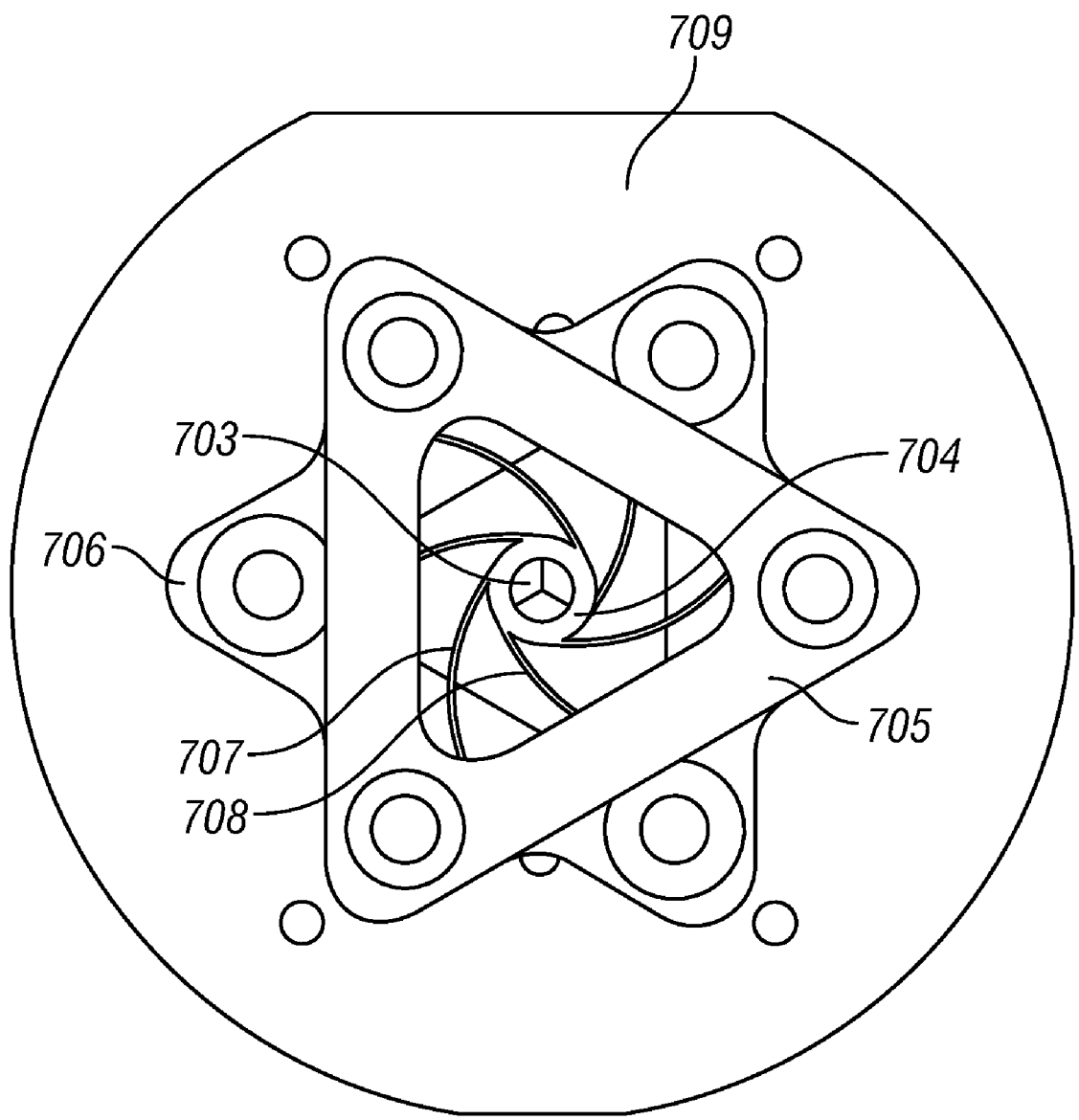
FIG. 17 is a bottom-side plan view of the indenter module of FIG. 16 after assembly.

FIG. 17 is a bottom-side plan view of the flexure of FIG. 16 after assembly. FIG. 18 is a plan view of the planar leaf springs of the flexure of FIG. 16. Such springs are fabricated using metals, including beryllium copper, and machining methods well-known to those versed in the art.

Figure 19:
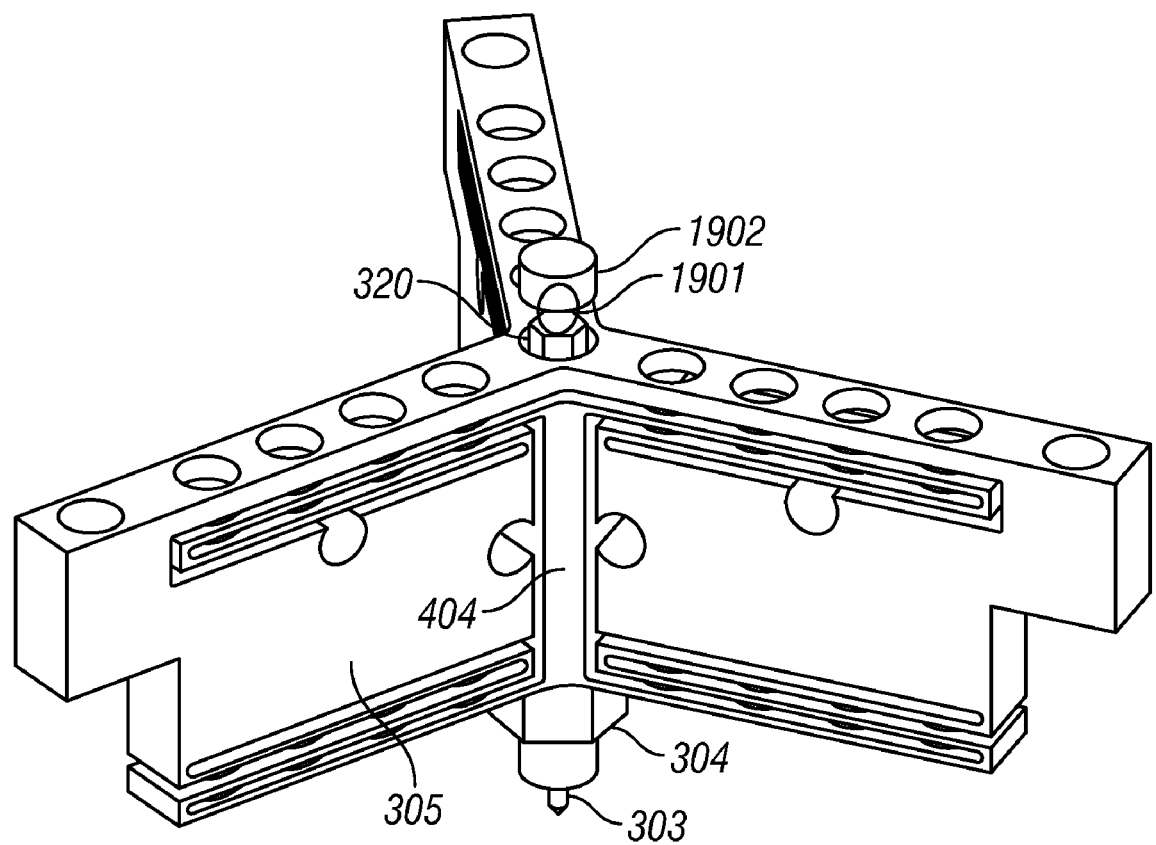
FIG. 19 is a perspective view of an optical lever detection system designed to substitute for the mechanical converter system depicted in FIG. 6.

FIG. 19 shows an optical lever detection system designed to free the modules embodying the current invention from the use of the mechanical converter assembly described above in order to access the optical lever detection system of an AFM. A mirror 1901 is attached to the collar 320 which is rigidly attached to central shaft 404, chuck 304 and indenter probe 303 of the flexure of the first preferred embodiment of the invention. Mirror 1901 deflects an incident light beam coming into the optical lever detection system and as this mirror moves relative to the indenter probe 303, a PSD of the optical lever detection system measures the displacement. An additional lens 1902 may be placed above mirror 1901 to increase sensitivity and facilitate calibration of the optical lever detection system.

The described embodiments of the invention are only considered to be preferred and illustrative of the inventive concept. The scope of the invention is not to be restricted to such embodiments. Various and numerous other arrangements may be devised by one skilled in the art without departing from the spirit and scope of the invention.

What is claimed is:

1. A nanoindenter, comprising:
   a module installed in an atomic force microscope which includes an actuator that is operable to actuate an indenter probe and an optical lever detection system that is operable to measure the motion of a flexure controlling the indenter probe;
   an indenter probe attached to a central shaft of a monolithic threedimensional leaf spring flexure which constrains the motion of such probe to the axis perpendicular to a sample; and
   a mechanical converter assembly which converts a z-axis motion of such central shaft to an angular change which is operable to measure such optical lever detection system.

* * * * *